United States Patent
Someya et al.

(10) Patent No.: US 10,413,242 B2
(45) Date of Patent: Sep. 17, 2019

(54) BIOCOMPATIBLE ELECTRODE STRUCTURE AND METHOD FOR MANUFACTURING THE SAME, AND DEVICE AND METHOD FOR MANUFACTURING THE SAME

(71) Applicant: Japan Science and Technology Agency, Kawaguchi-shi, Saitama (JP)

(72) Inventors: Takao Someya, Tokyo (JP); Tsuyoshi Sekitani, Osaka (JP); Remi Takano, Tokyo (JP)

(73) Assignee: JAPAN SCIENCE AND TECHNOLOGY AGENCY, Kawaguchi-shi (JP)

( * ) Notice: Subject to any disclaimer, the term of this patent is extended or adjusted under 35 U.S.C. 154(b) by 576 days.

(21) Appl. No.: 14/905,474

(22) PCT Filed: Jul. 18, 2014

(86) PCT No.: PCT/JP2014/069193
§ 371 (c)(1),
(2) Date: Jan. 15, 2016

(87) PCT Pub. No.: WO2015/008857
PCT Pub. Date: Jan. 22, 2015

(65) Prior Publication Data
US 2016/0155530 A1    Jun. 2, 2016

(30) Foreign Application Priority Data
Jul. 18, 2013  (JP) ................................ 2013-149663

(51) Int. Cl.
*A61B 5/00* (2006.01)
*A61L 27/50* (2006.01)
(Continued)

(52) U.S. Cl.
CPC ............ *A61B 5/6846* (2013.01); *A61B 5/686* (2013.01); *A61B 5/6867* (2013.01); *A61L 27/50* (2013.01);
(Continued)

(58) Field of Classification Search
CPC ... A61B 5/0408; A61B 5/0478; A61B 5/0492; A61L 27/50; A61L 2420/02;
(Continued)

(56) References Cited

U.S. PATENT DOCUMENTS

2006/0266981 A1* 11/2006 Asaka ................... B81B 3/0094
                                                          252/500
2009/0005667 A1    1/2009 Cui et al.
(Continued)

FOREIGN PATENT DOCUMENTS

EP       1693950 A1    8/2006
JP       H08-243085 A  9/1996
(Continued)

OTHER PUBLICATIONS

Japan Patent Office, Notice of Allowance for Japanese Application No. 2013-149663 (3 pp., 3 pp. English translation), dated Jan. 16, 2018.
(Continued)

*Primary Examiner* — Eun Hwa Kim
(74) *Attorney, Agent, or Firm* — Amster, Rothstein & Ebenstein LLP

(57) ABSTRACT

There is provided a biocompatible electrode structure which is capable of being connected to an electronic circuit, and in which a conductive nanomaterial is dispersed into a polymeric medium in which a density of the conductive nanomaterial on an opposite side of a connection surface to the (Continued)

electronic circuit, in the polymeric medium is lower than that on the side of the connection surface to the electronic circuit.

14 Claims, 8 Drawing Sheets

(51) Int. Cl.
*A61L 31/12* (2006.01)
*H01B 1/24* (2006.01)
*H05K 1/09* (2006.01)

(52) U.S. Cl.
CPC .............. *A61L 31/126* (2013.01); *H01B 1/24* (2013.01); *H05K 1/09* (2013.01); *A61B 2562/0214* (2013.01); *A61L 2400/12* (2013.01); *A61L 2420/02* (2013.01); *A61L 2420/04* (2013.01)

(58) Field of Classification Search
CPC .............. A61L 2420/04; A61L 2400/12; A61L 31/126; H01B 1/24; H05K 1/09
See application file for complete search history.

(56) References Cited

U.S. PATENT DOCUMENTS

| 2010/0016702 | A1* | 1/2010 | Greene | A61B 5/0408 600/391 |
|---|---|---|---|---|
| 2010/0244633 | A1 | 9/2010 | Nagai et al. | |
| 2012/0228558 | A1* | 9/2012 | Konishi | B82Y 10/00 252/510 |
| 2013/0209807 | A1 | 8/2013 | Chatterjee | |

FOREIGN PATENT DOCUMENTS

| JP | 09-075464 | A | 3/1997 |
|---|---|---|---|
| JP | 09-108195 | A | 4/1997 |
| JP | 2001-190694 | A | 7/2001 |
| JP | 3676337 | B2 | 5/2005 |
| JP | 4038685 | B2 | 11/2007 |
| JP | 2010515779 | A | 5/2010 |
| JP | 2011-513038 | A | 4/2011 |
| JP | 2011-528578 | A | 11/2011 |
| JP | 2011-530334 | A | 12/2011 |
| JP | 5106885 | B2 | 12/2012 |
| JP | 2013-034699 | A | 2/2013 |
| WO | 93/09713 | A1 | 5/1993 |
| WO | 2005/103664 | A2 | 11/2005 |
| WO | 2009101985 | A1 | 8/2009 |
| WO | 2009102077 | A1 | 8/2009 |
| WO | 2009/114689 | A1 | 9/2009 |
| WO | 2010/009385 | A1 | 1/2010 |
| WO | 2010/017276 | A2 | 2/2010 |
| WO | 2011055776 | A1 | 5/2011 |
| WO | 2011/157714 | A1 | 12/2011 |
| WO | 2012/087480 | A1 | 6/2012 |

OTHER PUBLICATIONS

Zhang Ya, Application of Ionic Liquids in Electrochemistry Chapter 6, Application of Ionic Liquids in Electrochemistry [M], pp. 102-105 (including two pages of partial English translation), 2009.
State Intellectual Property Office of People's Republic of China, Office Action for Chinese Application No. 201480039784.7 (8 pp., 3 pp. partial English Translation), dated Apr. 2, 2018.
Jonathan Viventi et al., "Flexible, foldable, actively multiplexed, high-density electrode array for mapping brain activity in vivo", Nature Neuroscience, vol. 14, No. 12, pp. 1599-1605 (Dec. 2011).
Quan Qing et al., "Nanowire transistor arrays for mapping neural circuits in acute brain slices", PNAS, vol. 107, No. 5, pp. 1882-1887 (Feb. 2, 2010).
Tsuyoshi Sekitani et al., "Flexible organic transistors and circuits with extreme bending stability", Nature Materials, vol. 9, pp. 1015-1022 (Dec. 2010).
International Search Report received for PCT Patent Application No. PCT/JP2014/069193 dated Aug. 12, 2014, 4 pages.
Japan Patent Office, Office Action for Japanese Application No. 2013-149663 (7 pp., 7 pp. English translation), Jun. 27, 2017.
State Intellectual Property Office of People's Republic of China, Office Action and Search Report for Chinese Application No. 201480039784.7 (8 pp., 12 pp. English translation), dated Jul. 12, 2017.
Jana Šefčovičová et al., "A biopolymer-based carbon nanotube interface integrated with a redox shuttle and a sorbitol dehydrogenase for robust monitoring of D-sorbitol," Microchimica Acta: An International Journal on Micro and Trace Analysis, vol. 175, No. 1-2, Jul. 7, 2011 (Jul. 7, 2011), pp. 21-30, Springer Vienna.
European Patent Office, "Extended European Search Report," issued in European Patent Application No. 14 826 299.1, which is a European Counterpart of U.S. Appl. No. 14/905,474, dated Feb. 23, 2017, 10 pages.

* cited by examiner

BIOCOMPATIBLE ELECTRODE STRUCTURE AND METHOD FOR MANUFACTURING THE SAME, AND DEVICE AND METHOD FOR MANUFACTURING THE SAME

BACKGROUND OF THE INVENTION

Field of the Invention

The present invention relates to a biocompatible electrode structure and a method for manufacturing the same, and a device and a method for manufacturing the same.

Priority is claimed on Japanese Patent Application No. 2013-149663, filed Jul. 18, 2013, the content of which is incorporated herein by reference.

Description of Related Art

Flexible electronics using an organic semiconductor have received attention in recent years, as means for installing a device that is configured by a soft material onto a surface or an inside of a living body, and obtaining biological information directly from a cell or a tissue. On the inside of the living body, an electrical contact with the tissue or the cell is mainly performed through metal such as Pt or Au (NPL 1 or NPL 2).

However, if the metal such as Pt or An is in contact directly with the tissue or the cell of the living body, since inflammatory response occurs between the metal and the tissue or the cell by antibody response of the biological cell, there is a problem such that it is difficult to perform a biological information observation in the long term. Moreover, undulation of the surface such as wrinkle is present on the surface of the biological cell, but there is the problem such that an electrode which is formed of the metal is generally hard, and may not follow a local change of a surface shape. Therefore, there is the problem such that the contact of the electrode becomes unstable, and an electrical signal becomes unstable. For these reasons, as an electrode material which is in contact directly with the biological cell, development of a material that has biocompatibility, and is excellent in followability of the surface shape which is capable of sufficiently covering the surface of the biological cell, is desired.

Meanwhile, a conductive nanomaterial such as carbon nanotube (CNT) is expected as a flexible conductive material. In PTL 1, a conductor material for an actuator element that is configured by a gel of the carbon nanotube and an ionic liquid, and is rich in flexibility, or an electrode layer for the actuator element that is configured by a gel composition of the carbon nanotube, the ionic liquid, and polymer is disclosed. It is assumed that at the time of forming the gel or the gel-shaped composition, by performing a subdivision treatment under the shearing force, entanglement of the mutual carbon nanotubes is reduced, and molecules of the ionic liquid which are bonded by "cation-π" interaction are formed on the surface of the carbon nanotube where the entanglement is reduced, by binding bunches of the carbon nanotubes to each other through ionic bond (PTL 2). Furthermore, the "cation-π" interaction has a strength which is equal to that of a hydrogen bond (approximately 10 times the Van der Waals force).

CITATION LIST

Patent Literature

[PTL 1] Japanese Patent No. 4038685
[PTL 2] Japanese Patent No. 3676337

Non-Patent Literature

[NPL 1] Jonathan VIenti et al Nature Neuroscience, 2011, Vol. 14, No. 12, 1599-1607
[NPL 2] Quan Qing et al., PNAS, 2010, Vol. 107, No. 5, 1882-1887

SUMMARY OF THE INVENTION

However, the understanding of an influence which the conductive nanomaterial such as the carbon nanotube (CNT) has on the living body is not sufficiently advanced, and the study of using the conductive nanomaterial such as the carbon nanotube (CNT) as a material of the device which is installed onto the surface of the living body or in the body is not advanced. Actually, in PTL 1 and PTL 2, since the material that is disclosed therein is not assumed to be used as a material of the device which is installed onto the surface of the living body or in the body, there is no description or suggestion of the electrode in a state where the influence which the conductive nanomaterial has on the living body is limited or of the device including the electrode.

In PTL 2, it is described that the molecules of the ionic liquid are bonded onto the surface of the carbon nanotube, but there is no description or suggestion of a configuration where the surface of the carbon nanotube is covered with the molecules of the ionic liquid, and a layer of the molecules of the ionic liquid is further covered with the polymer.

Moreover, in PTL 1, the electrode layer that is configured by the gel-shaped composition of the carbon nanotube, the ionic liquid, and the polymer is disclosed, but the polymer is mixed in order to maintain the mechanical strength (paragraph 0026 or the like), and it is merely disclosed that the electrode layer which is configured by the gel-shaped composition is obtained by a method for forming the electrode layer which is configured by the gel-shaped composition by heating and mixing the gel of the carbon nanotube and the ionic liquid with the polymer. Still more, there is no description or suggestion of a rinse process for making the molecules of the ionic liquid, which cover the carbon nanotube, into a monolayer, a rinse process for removing the molecules of the ionic liquid which are not bonded to the carbon nanotube, or a crosslinking process of crosslinking the polymer.

Additionally, a material dispersing the conductive nanomaterial into a polymeric medium is a material that has both of softness of the polymeric medium and conductivity of the conductive nanomaterial, but in a portion where the conductive nanomaterial is included, the original softness of the polymeric medium is damaged. Moreover, if the conductive nanomaterial is largely included in a portion which is in contact with the living body, there is a case where an inflammatory response occurs. On the other hand, if the conductive nanomaterial is small, there is a problem in that the impedance between the electrode and the device becomes large, or exchange of the information with good accuracy is not possible.

The present invention is made in consideration of the above circumstances, and an object thereof is to provide a biocompatible structure and a method for manufacturing the same, and a device and a method for manufacturing the same that have biocompatibility, and are capable of being inserted into the living body for a long period, and are capable of forming a very good interface between internal organs by being excellent in followability with respect to the shape of the wrinkle of the internal organ, and have low impedance throughout from a low frequency to a high frequency.

In order to achieve the above object, the present invention adopts the following means.

According to an aspect of the present invention, there is provided a biocompatible electrode structure which is capable of being connected to an electronic circuit, and in which a conductive nanomaterial is dispersed into a polymeric medium, in which a density of the conductive nanomaterial on an opposite side of a connection surface to the electronic circuit, in the polymeric medium is lower than that on the side of the connection surface to the electronic circuit.

In the biocompatible electrode structure according to the aspect of the present invention, the conductive nanomaterial is a carbon nanomaterial.

Moreover, in the biocompatible electrode structure according to the aspect of the present invention, the polymeric medium has a gel shape.

Still more, in the biocompatible electrode structure according to the aspect of the present invention, a second polymer layer that is configured by a second polymeric medium of which the amount of the conductive nanomaterial is small in comparison with a first polymeric medium, is arranged on a first polymer layer.

In the biocompatible electrode structure according to the aspect of the present invention, in the biocompatible electrode structure is formed by laminating a first polymer layer that is configured by a polymeric medium which includes the conductive nanomaterial, and the second polymer layer that is configured by a polymeric medium which does not include the conductive nanomaterial or includes the conductive nanomaterial at a density which is lower than that of the first polymer layer, in order from the side of the connection surface to the electronic circuit.

According to another aspect of the present invention, there is provided a device including the above biocompatible electrode structure as an electrode.

According to still another aspect of the present invention, a device which includes the above biocompatible electrode structure further includes a plurality of electrodes that are connected to the biocompatible electrode structure, in which the biocompatible electrode structure is arranged according to the plurality of electrodes.

Moreover, according to still another aspect of the present invention, there is provided a device which includes the above biocompatible electrode structure further includes a plurality of electrodes, in which each electrode is configured by the first polymer layer, and the second polymer layer is formed over the plurality of electrodes.

Still more, according to still another aspect of the present invention, a device includes the above biocompatible electrode structure further includes a plurality of electrodes, in which each electrode is configured by the first polymer layer and the second polymer layer.

According to still another aspect of the present invention, a device includes the above biocompatible electrode structure further includes a plurality of electrodes that are connected to the biocompatible electrode structure, in which the first polymer layer is arranged for each electrode, and the second polymer layer is formed over the plurality of electrodes.

Moreover, according to still another aspect of the present invention, a device includes the above biocompatible electrode structure further includes a plurality of electrodes that are connected to the biocompatible electrode structure, in which the first polymer layer and the second polymer layer are arranged for each electrode.

According to still another aspect of the present invention, there is provided a method for manufacturing the biocompatible electrode structure including a step of forming a liquid film where the conductive nanomaterial is dispersed into a polymeric medium, on an electronic circuit which includes a plurality of electrodes, a step of unevenly distributing the conductive nanomaterial on the electronic circuit side, and a step of arranging the biocompatible electrode structure on each electrode by curing the liquid film.

According to still another aspect of the present invention, there is provided a method for manufacturing the biocompatible electrode structure including a step of forming a first polymeric medium that constitutes the first polymer layer which includes a conductive nanomaterial, on an electronic circuit which includes a plurality of electrodes, a step of forming a second polymeric medium that constitutes the second polymer layer which does not include the conductive nanomaterial or includes the conductive nanomaterial at a density which is lower than that of the first polymer layer, on the first polymeric medium, and a step of collectively processing the first polymeric medium and the second polymeric medium so as to be arranged on each electrode.

According to still another aspect of the present invention, there is provided a method for manufacturing the device including a process of forming a first polymeric medium that constitutes the first polymer layer which includes the conductive nanomaterial, on an electronic circuit, a process of forming a second polymeric medium that constitutes the second polymer layer which does not include the conductive nanomaterial or includes the conductive nanomaterial at a density which is lower than that of the first polymer layer, on the first polymeric medium, and a process of collectively processing the first polymeric medium and the second polymeric medium so as to form a plurality of electrodes on the electronic circuit.

According to still another aspect of the present invention, there is provided a method for manufacturing the device including a process of forming a first polymeric medium that becomes the first polymer layer which includes the conductive nanomaterial, on an electronic circuit which includes a plurality of electrodes, a process of forming a second polymeric medium that becomes the second polymer layer which does not include the conductive nanomaterial or includes the conductive nanomaterial at a density which is lower than that of the first polymer layer, on the first polymeric medium, and a process of collectively processing the first polymeric medium and the second polymeric medium so as to be arranged on each electrode.

According to the biocompatible electrode structure according to the aspect of the present invention, since a configuration where the conductive nanomaterial is dispersed with high density on the connection surface side to the electronic circuit, and is dispersed at the density which is lower than that of the connection surface on the opposite side in the polymeric medium, that is, a configuration where the conductive nanomaterial of the side which is in contact with the surface or the tissue of the living body is dispersed at the density which is lower than the density of the connection surface side to the electronic circuit is adopted, it is possible to limit the inflammatory response of the living body. Moreover, since the density of the conductive nanomaterial of the side which is in contact with the surface or the tissue of the living body is low, the biocompatible electrode structure of the present invention can have the original softness of the polymeric medium, and can be evenly stuck to a matter (here, the surface or the tissue of the living body) which is made into a target. Thereby, since a substantial contact area of the biocompatible electrode structure with the surface or the tissue of the living body becomes large, it is possible to make the impedance even lower with respect to the electrical signal of the high frequency. Therefore, by making the contact area large, it is possible to noticeably enhance detection sensitivity of the electrical signal in comparison with a case by a metallic material of the related art. Consequently, it is possible to further miniaturize the electrode. Still more, by making the density of the conductive nanomaterial on the connection surface side to the electronic circuit be high, it is possible to suppress an increase of the impedance with respect to the electrical signal of the low frequency due to capacitive coupling to be low.

In the related art, as a stimulating electrode of a pacemaker, there is a case which may be inserted into the living body for a long period in the electrode which gives stimulus to the internal organ or the like in the living body, but there is no case which may be inserted into the living body for the long period in the electrode that reads out the electrical signal which comes out from the internal organ or the like in the living body. This results from that if the electrode which is manufactured by the material of the related art is put into the living body, shortly, foreign matter response (inflammatory response) occurs between the electrode and the tissue of the internal organ or the like, and it is difficult to detect the electrical signal. Even if such the foreign matter response occurs in the electrode which gives the stimulus, it is possible to accomplish the object of giving the stimulus, but in the electrode that detects the electrical signal which is emitted by the internal organ or the like in the living body, it is difficult to accomplish the object of detecting the electrical signal. On the contrary, the biocompatible electrode structure of the present invention can be stored in the living body for the long period, and can be used in an electrode that stably reads out the electrical signal which is emitted by the internal organ or the like in the living body for a long period.

In this manner, the biocompatible electrode structure of the present invention can be used as a material of the electrode for a living body where the antibody response is small at the time of being put into the living body for the long period, and reliability is high. Moreover, since the biocompatible electrode structure of the present invention is very soft, it is possible to cover the surface of a biological tissue, without hurting the biological tissue. Still more, there is a cell tissue of approximately several 100 μm, but since the biocompatible electrode structure of the present invention can perform photocrosslinking, it is possible to manufacture a fine electrode of a size which may be applied to a predetermined cell tissue.

Additionally, the electrode which is manufactured by the biocompatible electrode structure of the present invention, can stably read out the signal of the internal organ for the long period by being stuck to the internal organ or the like in the living body. If a weak signal from the living body is not amplified, the detection is difficult, but by including a soft amplifier that is manufactured by using an organic transistor (for example, NATURE MATERIALS, 9, 2010, 1015 to 1022) near the internal organ, it is possible to amplify the electrical signal from the internal organ or the like. Thereby, it is possible to bring out a very weak electrical signal with high accuracy, and it is possible to detect the weak signal from the living body.

According to the method for manufacturing the biocompatible electrode structure according to the aspect of the present invention, since a configuration including the process of collectively processing the first polymeric medium that constitutes the first polymer layer which includes the conductive nanomaterial, and the second polymeric medium that constitutes the second polymer layer which does not include the conductive nanomaterial or includes the conductive nanomaterial at the density which is lower than that of the first polymer layer so as to be arranged on each electrode is adopted, it is possible to easily adjust the impedance of the biocompatible electrode structure only by changing the density of the conductive nanomaterial or a thickness of the polymer layer.

BRIEF DESCRIPTION OF THE DRAWINGS

FIG. 9A is a photograph showing a state after a case where the carbon nanotube is put into deionized water, and is stirred for one week, and FIG. 9B is a photograph showing a state after a case where the carbon nanotube and DEMEBF$_4$ are put into the deionized water, and are stirred for one week in the same manner, and FIG. 9C is a photograph showing a state after a case where the carbon nanotube is put into the deionized water, and is stirred for one week in the same manner, and thereafter, is treated in the jet mill, and FIG. 9D is a photograph showing a state after a case where the carbon nanotube and DEMEBF$_4$ of 60 mg are put into the deionized water, and are stirred for one week in the same manner, and thereafter, are treated in the jet mill, and FIG. 9E is a photograph showing a state after a case where the carbon nanotube, DEMEBF$_4$, and microfibrillated cellulose are put into the deionized water, and are stirred for one week in the same manner, and thereby, a paste is obtained, and thereafter, is treated in the jet mill.

DETAILED DESCRIPTION OF THE INVENTION

Figure 1:
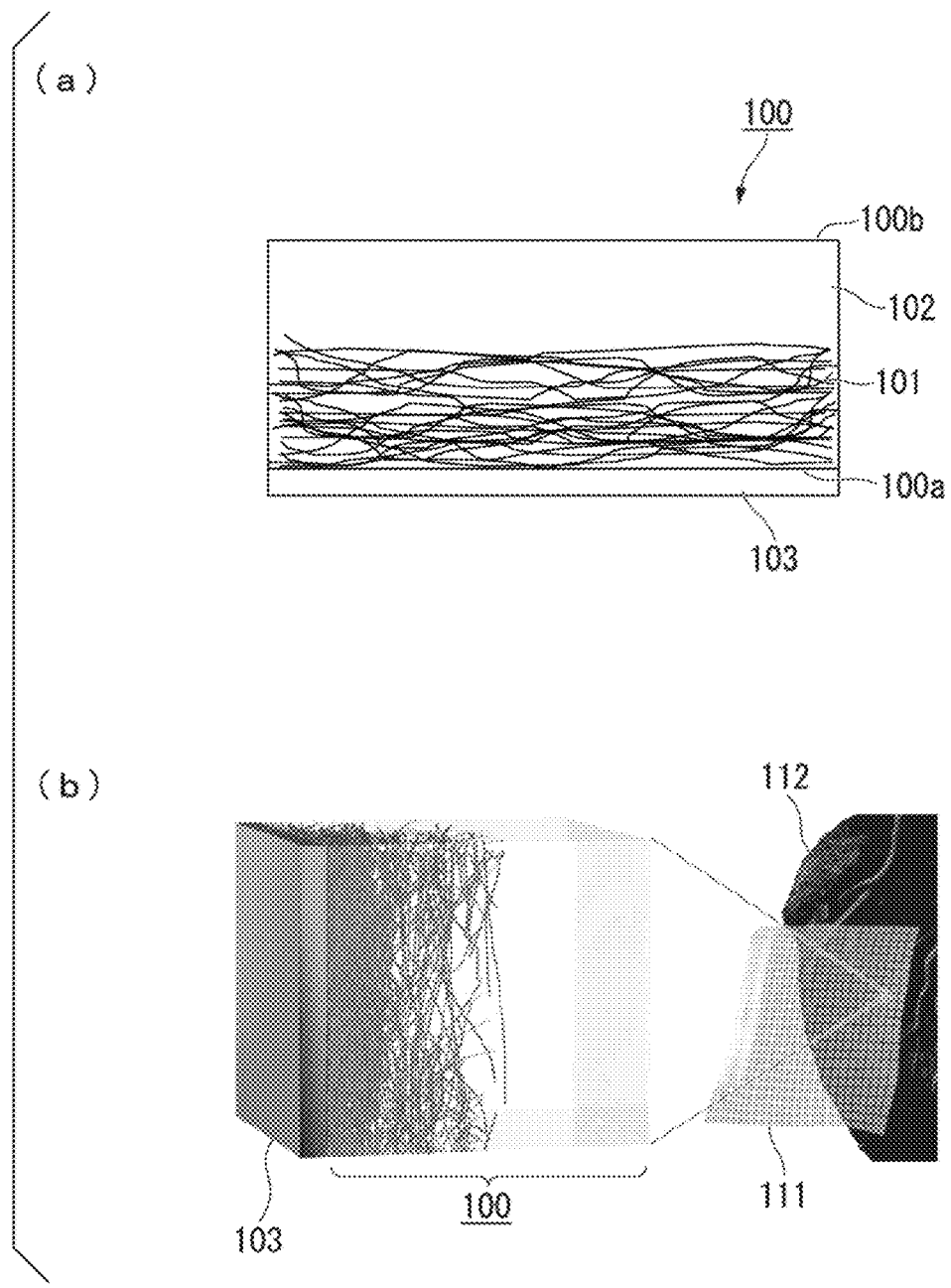
FIG. 1(a) is a sectional view schematically showing a configuration of a biocompatible electrode structure according to a first embodiment of the present invention.
FIG. 1(b) is a diagram schematically showing a portion of a device that includes the biocompatible electrode structure of the present invention on an electrode.

Hereinafter, the present invention will be described with reference to the drawings, based on suitable embodiments. Furthermore, the embodiments described hereinafter, use examples in order to understand the gist of the invention better, and are not to limit the present invention unless designated in particular. Moreover, in the drawings that are used in the following description, in order to easily understand features of the present invention, for convenience, there are cases where a portion which becomes a main portion is enlarged, and dimensional ratios of the respective components are not necessarily the same as the actual ratios.

Biocompatible Electrode Structure (First Embodiment)

A configuration of a biocompatible electrode structure 100 according to a first embodiment of the present invention, will be described by using FIG. 1(a). Moreover, an application example of the biocompatible electrode structure will be described by using FIG. 1(b). FIG. 1(a) is a sectional view schematically showing the configuration of the biocompatible electrode structure 100, and FIG. 1(b) is a diagram schematically showing a portion of an example of a device that includes the biocompatible electrode structure. The left side diagram is a schematic view of a case where one electrode of a biological tissue surface side of the device, and a portion of the biocompatible electrode structure which is arranged thereon are enlarged.

The biocompatible electrode structure 100 shown in FIG. 1(a), is a biocompatible electrode structure which is capable of being connected to an electronic circuit, and in which a conductive nanomaterial 101 is dispersed into a polymeric medium 102, and a density of the conductive nanomaterial 101 on an opposite surface 100b side of a connection surface to the electronic circuit in the polymeric medium 102 is lower than that on the side of the connection surface to the electronic circuit.

Reference sign 103 is an electrode of the electronic circuit, and FIG. 1(a) illustrates a state where the biocompatible electrode structure 100 is arranged on the electrode 103.

In FIG. 1(b), the configuration where a plurality of electrodes 103 are formed on an insulating sheet 111, and the biocompatible electrode structure 100 is arranged on the electrodes 103, and the biocompatible electrode structure 100 is arranged so as to be stuck onto a surface of a biological tissue 112, is schematically shown.

In the device shown in FIG. 1(b), by the electronic circuit (not shown) which is formed on the insulating sheet, it is possible to give stimulus to the biological tissue through the biocompatible electrode structure, or to detect a signal of a living body.

The "conductive nanomaterial" of the present invention is a material that is configured by the component with nanometer size.

The "conductive nanomaterial" of the present invention is preferably a carbon nanomaterial.

The carbon nanomaterial is a material in which in the component (for example, one CNT) that is configured by carbon atoms, and is structured in the nanometer size, generally, the carbon atoms of the component are stuck to each other by Van der Waals force, and is, for example, a carbon nanotube, a carbon nanofiber (carbon fibers having diameter of 10 nm or less), carbon nanohorn, fullerene or graphene. A fine carbon nanomaterial of 10 nm or less exhibits good dispersibility in water.

Other examples of a "conductive nanomaterial" include nanoparticles such as gold, platinum or silver nanoparticles, or PEDOT/PSS particles.

In the carbon nanomaterial, only one type may be used, or a plurality of types may be used.

The carbon nanotube is carbon nanotube that has a structure in which a graphene sheet in which the carbon atoms are arranged into a hexagonal mesh shape, is rounded into a cylindrical shape by a single wall or multiple walls (referred to as single-walled nanotube (SWNT), double-walled nanotube (DWNT) or multi-walled nanotube (MWNT)), but the carbon nanotube that may be used as a carbon nanomaterial is not particularly limited, and there is no problem with the carbon nanotube being any of SWNT, DWNT, and MWNT. Moreover, the carbon nanotube may in general be manufactured by a laser ablation method, are discharge, a thermal CVD method, a plasma CVD method, a gas phase method, a combustion method or the like, but there is no problem with the carbon nanotube being manufactured by another method. Still more, there is no problem with a plurality of types of carbon nanotubes being used.

The carbon nanotubes are apt to be aggregated by Van der Waals force between the carbon nanotubes, and generally, a plurality of carbon nanotubes form a bundle (bunch) or forming an aggregate. However, under the presence of an ionic liquid, it is possible to subdivide the bundle or the aggregate by adding a shearing force thereto (to reduce entanglement of the carbon nanotubes). By sufficiently performing the subdivision, it is possible to separate the carbon nanotubes into individual carbon nanotubes by weakening the Van der Waals force which makes the carbon nanotubes stick to each other, and it is possible for the ionic liquid to adsorb each of the carbon nanotubes, and as a result, it is possible to obtain a composition that includes the single carbon nanotube which is covered with molecules of the ionic liquid, and is configured by the carbon nanotubes and the ionic liquid.

Furthermore, means for applying the shearing force which is used in a subdivision process is not particularly limited, and it is possible to use a wet milling apparatus such as a ball mill, a roller mill, or a vibration mill which is capable of applying the shearing force.

It is considered that the carbon nanotube and the ionic liquid are mixed, and the subdivision process is performed, and thereby, the molecules of the ionic liquid which are bonded by "cation-π" interaction on the surface of the carbon nanotube where the entanglement is reduced, become a gel-shaped (gel, gel-like) composition by binding the carbon nanotubes to each other through ionic bond (PTL 2), but as described later, for example, by rinsing the gel-shaped composition with physiological saline or ethanol, it is possible to form a layer of the molecules of the ionic liquid of one layer on the surface of the carbon nanotube, and further, by mixing the water with water-soluble polymer, it is possible to manufacture a composition in which the carbon nanotube which is covered with the molecules configuring the ionic liquid is dispersed into a water-soluble polymeric medium.

The "polymeric medium" of the present invention is not particularly limited, as long as it is a polymer which disperses the conductive nanomaterial. The "polymeric medium" of the present invention is preferably a gel.

For example, when the water-soluble polymer (medium) is used as a polymeric medium, it is not particularly limited as long as it dissolves or disperses in water, and it is more preferably crosslinked in water. For example, it is possible to use the following examples.

1. Synthetic Polymer
(1) Ionic Properties
  polyacrylic acid (anionic properties)
  polystyrene sulfonic acid (anionic properties)
  polyethyleneimine (cationic properties)
  MPC polymer (amphoteric ion)
(2) Non-Ionic Properties
  polyvinyl pyrrolidone (PVP)
  polyvinyl alcohol (polyvinyl acetate saponified substance)
  polyacrylamide (PAM)
  polyethylene oxide (PEO)
2. Natural System Polymer (Mostly, Polysaccharide)
  starch
  gelatin
  hyaluronic acid
  alginic acid
  dextran
  protein (for example, water-soluble collagen or the like)
3. Semisynthetic Polymer (for Example, Cellulose which is Solubilized)
  cellulose derivative such as
  carboxymethyl cellulose (CMC)
  hydroxypropyl cellulose (HPC) or
  methylcellulose (MC)
  water-soluble chitosan (which may be classified into "2. Natural System Polymer")

Moreover, as a specific compound of the water-soluble polymer, for example, it is possible to use polyrotaxane. Polyrotaxane is formed by arranging a capping group, so that cyclic molecule is not isolated, at both ends (both ends of a straight chain molecule) of pseudo-polyrotaxane which is made such that an opening portion of the cyclic molecule (rotator) is clathrated into a skewer shape by the straight chain molecule (axis). For example, it is possible to use polyrotaxane which uses α-cyclodextrin as a cyclic molecule, and polyethylene glycol as a straight chain molecule.

Still more, a compound has a group which reacts to a crosslinking agent as a water-soluble polymeric medium is more preferable for forming a strong film by the crosslinking.

By using the biocompatible electrode structure of the present invention, in forming a pattern of a fine shape, it is preferable that the water-soluble polymer have photocrosslinking properties.

The polymeric medium may be a polymeric medium which is cured by energy deposition (heat, light, electron beam or the like).

The biocompatible electrode structure of the present invention is not particularly limited to being applied to a living body, and may be applied to any field where effects thereof are exhibited.

The biocompatible electrode structure of the present invention may be arranged on the electrode on the electronic circuit, or may be used as an electrode itself on the electronic circuit. In the biocompatible electrode structure of the present invention, by containing the conductive nanomaterial so as to be unevenly distributed on the connection surface side to the electronic circuit, since it is possible to make the impedance of the electronic circuit very small, it is possible to accurately transmit a biological signal to the electronic circuit.

(Biocompatible Electrode Structure Including Doubly Covered Carbon Nanomaterial)

When the carbon nanomaterial is used as a conductive nanomaterial, the carbon nanomaterial may be doubly covered with the molecules configuring the hydrophilic ionic liquid, and the water-soluble polymer. That is, the biocompatible electrode structure may be made by dispersing the carbon nanomaterial which is doubly covered with the molecules configuring the hydrophilic ionic liquid, and the water-soluble polymer into the polymeric medium.

The study of the influence which the ionic liquid has on the living body is not sufficiently advanced, but since the biocompatible electrode structure has a configuration of being doubly covered by covering the molecules that configure the ionic liquid which is bonded to the carbon nanomaterial with the water-soluble polymer, it is possible to avoid the molecules configuring the ionic liquid from touching a living body even when the configuration is used in the situation of touching the living body. Moreover, since the carbon nanomaterial main body (carbon nanomaterial itself before being covered with the molecules configuring the ionic liquid, and the water-soluble polymer) is doubly covered with the molecules configuring the ionic liquid, and the water-soluble polymer, it is possible to avoid the carbon nanomaterial main body from touching a living body even when the configuration is used in the situation of touching the living body.

Regarding the material configuring the biocompatible electrode structure, in accordance with the international standard ISO 10993-6 relating to biocompatibility, it was confirmed that no cytotoxicity was present by carrying out a "cytotoxicity test by a colony forming method", and further, it was confirmed that rejection symptoms by a living body were small in comparison with an Au electrode of the related art by carrying out a "rabbit implantation test" by the standard.

The above "doubly covered" means being covered with a layer of the molecules configuring the ionic liquid, and a layer of the water-soluble polymer. In the biocompatible electrode structure, since the carbon nanomaterial which is covered with the layer of the molecules of the ionic liquid, the water-soluble polymer, and the water are mixed, and the layer of the molecules of the ionic liquid is covered in the state where the water-soluble polymer is dissolved in water, that is, in a state where the water-soluble polymer is dispersed by being made into a small size, the water-soluble polymer is also covered by being made into a layer shape. On the contrary, in case of "the electrode layer that is configured by the gel-shaped composition of the carbon nanotube, the ionic liquid, and the polymer" which is described in PTL 1, since the electrode layer was formed by heating and mixing the gel of the carbon nanotube and the ionic liquid, and the polymer (Example 1 or the like), even if the molecules of the ionic liquid cover the carbon nanotube, the polymer does not cover the carbon nanotube (through the molecules of the ionic liquid).

Moreover, since the molecules configuring the ionic liquid, and the water-soluble polymer cover the carbon nanomaterial in the layer shape, the biocompatible electrode structure may be covered with the layer of the molecules configuring the ion liquid of substantially uniform thickness, and the layer of the water-soluble polymer of substantially uniform thickness. That is, in comparison with the gel composition which is described in PTL 1, it is possible to uniformly coat the carbon nanomaterial, which is represented by the carbon nanotube, at a molecular level. Still more, since the molecules of the ionic liquid are tightly bonded to the carbon nanomaterial, it is possible to perform the coating and the cover of the ionic liquid does not include pinhole.

The "substantially uniform thickness" of the layer of the molecules configuring the ionic liquid, is referred to as that the layer of the molecules configuring the ionic liquid of 70% or more, preferably, 90% or more is a monomolecular layer.

Additionally, the "substantially uniform thickness" of the layer of the water-soluble polymer, is referred to as that a deviation in the thickness of the layer of the water-soluble polymer of 70% or more, preferably, 90% or more, is 20 nm or less, and is preferably 10 nm or less, and is more preferably 5 nm or less.

The layer of the molecules of the ionic liquid which covers the carbon nanomaterial, may be the monomolecular layer. The surface of the carbon nanomaterial, and the molecules of the ionic liquid are bonded by "cation-$\pi$" interaction, but by selecting a combination of the carbon nanomaterial and the ionic liquid in which the bonding between the molecules of the ionic liquid is smaller than the boding by "cation-$\pi$" interaction, it is possible to make the layer of the molecules of the ionic liquid which wraps up the carbon nanomaterial into the monomolecular layer.

For example, by selecting the carbon nanotube as the carbon nanomaterial, and N,N-diethyl-N-methyl-N-(2-methoxyethyl) ammonium tetrafluoroborate ($DEMEBF_4$) as an ionic liquid, it is possible to make a layer of the molecules of $DEMEBF_4$ which wraps up the carbon nanotube into the monomolecular layer. Furthermore, for example, if polyrotaxane is selected as a water-soluble polymer, it is possible to form a thin polyrotaxane layer of approximately 5 nm on the monomolecular layer of $DEMEBF_4$. In the composition which is obtained in this manner, it is possible to achieve a highly dense dispersion concentration of carbon nanotubes, and it is possible to make a material of high conductivity. In a conductive member such as an electrode which is manufactured from a material with such conductivity, electrons move between the carbon nanotubes through the thin $DEMEBF_4$ molecular layer and polyrotaxane layer, and thereby, the current flows.

In the biocompatible electrode structure, since the surface of the carbon nanomaterial, and the molecules of the ionic liquid are strongly bonded by "cationic-$\pi$" interaction, the molecules of the ionic liquid which are bonded onto the surface of the carbon nanomaterial, do not come out outside of the water-soluble polymeric medium. Furthermore, for example, the molecules of the ionic liquid which are not bonded onto the surface of the carbon nanomaterial, may be removed by being rinsed with physiological saline or ethanol.

By adjusting the quantity of the hydrophilic ionic liquid into a quantity which can cover all of the carbon nanomaterial, the configuration where first, the carbon nanomaterial is completely covered with the molecules of the ionic liquid, and is covered with the water-soluble polymer thereon, is made.

The water-soluble polymer which covers the carbon nanomaterial through the molecules of the ionic liquid, and the water-soluble polymer (medium) into which the covered carbon nanomaterial is dispersed may be the same sorts, or may be the different sorts. For example, the configuration may be obtained by mixing the carbon nanomaterial which is covered with the molecules of the ionic liquid, the water-soluble polymer, and the water, and covering the carbon nanomaterial with the water-soluble polymer through the molecules of the ionic liquid, and subsequently, mixing the carbon nanomaterial which is covered with the water-soluble polymer through the molecules of the ion liquid, and the water-soluble polymer of the same sort or the different sort, and the water.

In the biocompatible electrode structure, the carbon nanomaterial may be covered with a monomolecular film of the molecules configuring the ionic liquid.

The surface of the carbon nanomaterial is covered by being bonded to the molecules of the ionic liquid, and the molecules of the ionic liquid which are not bonded onto the surface of the carbon nanomaterial are removed by being rinsed (performing the rinsing), and thereby, the carbon nanomaterial is covered with the monomolecular film of the molecules configuring the ionic liquid.

In the biocompatible electrode structure, even if being inserted into a living body, the carbon nanomaterial itself does not substantially touch a cell in the living body (alternatively, the area touching the cell is greatly reduced). Moreover, since it has high flexibility, it is possible to form a very good interface among the internal organs, which is excellent in followability with respect to the surface of an internal organ or the like in a living body. Furthermore, by adjusting the content of the carbon nanomaterial it is possible to make a carbon nanomaterial which has high conductivity. Still more, by making the molecules of the ionic liquid which cover the carbon nanomaterial into a monomolecular film, it is possible to make the conductivity between the carbon nanomaterials high. By making the water-soluble polymer which covers the carbon nanomaterial through the molecules of the ionic liquids, and the water-soluble polymer (medium) into which the covered carbon nanomaterial is dispersed of different types, it is possible to cure only one thereof.

In the related art, as a stimulating electrode of a pacemaker, there is a case which may be inserted into the living body for a long period in the electrode which gives stimulus to the internal organ or the like in a living body, but there are no cases where an electrode may be inserted into a living body for a long period to read out an electrical signal which comes out from the internal organ or the like in the living body. If an electrode which is manufactured by the material of the related art is put into a living body, it shortly results in a foreign matter response (inflammatory response) occurring between the electrode and the tissue of the internal organ or the like, and it is difficult to detect the electrical signal. Even if such the foreign matter response occurs in an electrode which gives the stimulus, it is possible to accomplish the object of giving the stimulus, but in the electrode that detects the signal of the internal organ or the like in the living body, it is difficult to accomplish the object of detecting the signal.

However, the biocompatible electrode structure may be stored in the living body for the long period. The biocompatible electrode structure is a material that may be used in an electrode which stably reads out the electrical signal which comes out from the internal organ or the like in the living body for the long period, or may be used by being arranged on the electrode.

In this manner, the biocompatible electrode structure may be used as a material of the electrode for the living body where the antibody response is small even if it is put into a living body for the long period, and the reliability thereof is high. Moreover, since the biocompatible electrode structure is very soft, it is possible to cover the surface of the biological tissue, without hurting the biological tissue. Still more, there is a cell tissue of approximately several 100 μm, but since the photocrosslinking is possible in the biocompatible electrode structure, it is suitable in manufacturing a fine electrode which may be applied to the cell tissue.

Additionally, since the electrode which is configured of the biocompatible electrode structure may stably read out the signal of the internal organ or the like for a long period by being stuck to the internal organ or the like in the living body, it is possible to amplify the signal from the internal organ or the like, near the internal organ by using an organic transistor (for example, NATURE MATERIALS, 9, 2010, 1015 to 1022). Thereby, it is possible to bring out a very weak signal with high accuracy. That is, if the weak signal from the living body is not amplified, the detection is difficult, but a soft amplifier that is manufactured from the organic transistor, and the electrode that is manufactured by the biocompatible electrode structure are used, and the weak signal from the living body is amplified in the vicinity of the internal organ or the like in the living body, and thereby, it is possible to detect a weak signal from the living body.

Moreover, at the time of detecting the electrical signal of the internal organ or the like due to capacitive coupling, the size is proportional to the surface area of the electrode. When the electrical signal is detected due to the capacitive coupling by using the electrode which is configured by the biocompatible electrode structure, since the electrode is particularly soft if being compared with a metal electrode of the related art, and may be tightly stuck to the internal organ or the like, the substantial contact area increases. Therefore, detection sensitivity of the substantial capacity for obtaining the electrical signal is very high in comparison with the metal electrode of the related art, and it is possible to further miniaturize the electrode. Moreover, since the carbon nanomaterial having high specific surface area is included, the biocompatible electrode structure has the signal detection ability which is high from this point. By containing the carbon nanomaterial, since it is possible to make the impedance of the electronic circuit be very small, it is possible to accurately transmit the biological signal to the electronic circuit.

Biocompatible Electrode Structure (Second Embodiment)

Figure 2:
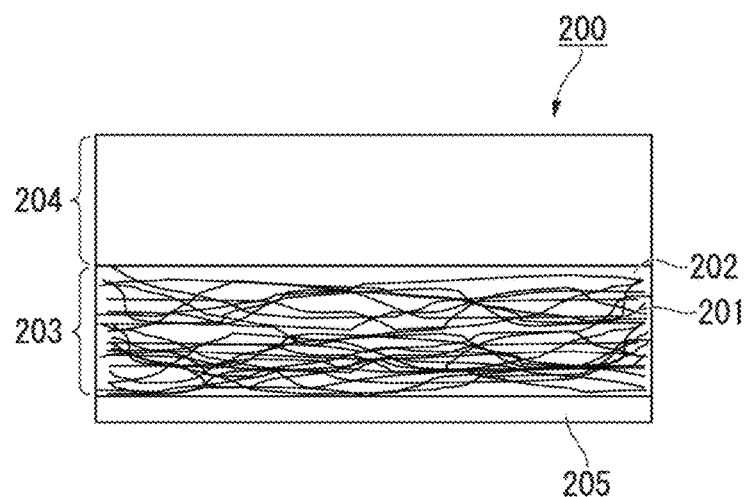
FIG. 2 is a sectional view schematically showing a configuration of a biocompatible electrode structure according to a second embodiment of the present invention.

FIG. 2 is a schematic view of a biocompatible electrode structure according to a second embodiment of the present invention.

In the following description, there is a case where the contents which are described in the biocompatible electrode structure according to the first embodiment will be omitted if being also applied to the present embodiment, and moreover, there is a case of being applied to the biocompatible electrode structure according to the first embodiment.

A biocompatible electrode structure 200 shown in FIG. 2, is a biocompatible electrode structure which is capable of being connected to the electronic circuit, and in which the conductive nanomaterial is dispersed into the polymeric medium, and is formed by laminating a first polymer layer 203 that is configured by a polymeric medium 202 which includes a conductive nanomaterial 201, and a second polymer layer 204 that is configured by the polymeric medium which does not include the conductive nanomaterial or includes the conductive nanomaterial at the density which is lower than that of the first polymer layer, in order from the side of the connection surface to the electronic circuit.

In the embodiment, by making a two-layer structure in which the polymer layer of which the conductive nanomaterial is at high density, and the polymer layer of which the conductive nanomaterial is at the low density or is not contained are sequentially stacked from the connection surface side to the electronic circuit, the configuration of being unevenly distributed so that the density of the conductive nanomaterial is higher than an opposite side thereof on the connection surface side to the electronic circuit in the polymeric medium, is made.

In this manner, by making a configuration in which the density of the conductive nanomaterial of the polymeric medium is unevenly distributed, the transmission of an alternating current signal is improved.

Regarding the two-layer structure which is configured by the polymeric mediums of two sorts according to the present invention (when the conductive nanomaterial is a carbon nanotube), one layer of the polymeric medium which does not include the carbon nanotube as a comparative example (Comparative Example 1), and one layer of the polymeric medium which includes the carbon nanomaterial at the low density and uniformly in comparison with the first polymer layer of the present invention (Comparative Example 2), if the frequency characteristic of the impedance is tested by stacking the layers on the Au electrode, in Comparative Examples, the impedance becomes high at low frequencies, and in contrast thereto, in the two-layer structure according to the present invention, the impedance was not nearly changed at low frequencies.

On the side of one layer of the polymeric medium which does not include the conductive nanomaterial (Comparative Example 1), it is considered that the frequency characteristics of the impedance of a capacitor are described with the polymeric medium acting as a capacitor. Moreover, even in one layer of a polymer gel which includes the conductive nanomaterial at a low density (Comparative Example 2), the frequency characteristics of the impedance are shown in the same manner as Comparative Example 1, and the action of the polymeric medium as a capacitor is increased in size in the illustration. In Comparative Example 1 and Comparative Example 2, there is no difference between the frequency characteristics or the difference is small, but since the carbon nanotube is included in the polymer layer of Comparative Example 1, to that extent, it is considered that the resistance itself is lower than that of the polymer layer of Comparative Example 2.

On the contrary, in the polymeric medium of the two-layer structure according to the present invention, the second polymer layer acts as a capacitor in the same manner as Comparative Example 1, and meanwhile, the first polymer layer is in charge of electrical characteristics such that the capacitor and a resistor are arranged in parallel, and thereby, it is assumed that the increase of the impedance at the low frequency is limited. The action as a capacitor is necessary in the transmission of the alternating current signal, and meanwhile, it is considered that the first polymer layer which includes the conductive nanomaterial at a high density plays an important role in the limiting the increase of the impedance at low frequencies. Moreover, by including the first polymer layer which contains the conductive nanomaterial on the connection surface side to the electronic circuit, since it is possible to make the impedance of the electronic circuit very small, it is possible to accurately transmit the biological signal to the electronic circuit.

Still more, it is considered that ion conduction particularly contributes to the electrical characteristics of the second polymer layer.

Method for Manufacturing Biocompatible Electrode Structure (First Embodiment)

A method for manufacturing the biocompatible electrode structure of the present invention includes a step of forming a liquid film which is configured by the polymeric medium and the conductive nanomaterial dispersed into the polymeric medium, on the electronic circuit which includes the plurality of electrodes, a step of unevenly distributing the conductive nanomaterial of the polymeric medium on the electronic circuit side, and a step of arranging the biocompatible electrode structure on each electrode by curing the liquid film.

The electronic circuit may use an electronic circuit which is formed on a sheet-shaped substrate.

The biocompatible electrode structure itself may be manufactured and used as an electrode.

For example, the step of forming the liquid film may be performed by a method including a first step of obtaining a first dispersed system which mixes the hydrophilic ionic liquid, the carbon nanomaterial (conductive nanomaterial), and the water, and in which the carbon nanomaterial that is covered with the molecules configuring the ionic liquid is dispersed, and a second step of obtaining a second dispersed system which mixes the first dispersed system, the water-soluble polymer, and the water, and in which the carbon nanomaterial that is covered with the molecules configuring the ionic liquid, and the water-soluble polymer are dispersed.

In the second dispersed system, by using a plurality of types of water-soluble polymers, it is possible to classify the water-soluble polymer which covers the carbon nanomaterial through the molecules of the ionic liquid, and the water-soluble polymer (medium) into which the covered carbon nanomaterial is dispersed into the different types. Alternatively, it is possible to classify the water-soluble polymer which covers the carbon nanomaterial through the molecules of the ionic liquid into a plurality of types. Thereby, the hardness adjustment of the material, or the control of conductivity optical characteristics or the like, is possible.

As a method for unevenly distributing the conductive nanomaterial of the polymer layer on the electronic circuit side, for example, a method in which the carbon nanomaterial (conductive nanomaterial) is covered using a magnetic ionic liquid as a hydrophilic ionic liquid, and a magnet is used from below the electronic circuit (substrate where the electronic circuit is formed), and the carbon nanomaterial which is covered with the magnetic ionic liquid is attracted onto the electronic circuit side of the polymer layer, or a method in which the polymer gel layers of the different conductive nanomaterials are stacked in a plurality of layers, is used.

The method for manufacturing the biocompatible electrode structure may be subdivided by adding the shearing force to carbon nanomaterial, in the first step. Thereby, it is possible to cover the bundle or the aggregate of the carbon nanomaterials with the hydrophilic ionic liquid in the state of being further loosened.

The method of manufacturing the biocompatible electrode structure, may further include a step of manufacturing the biocompatible electrode structure in which after the second step, the water-soluble polymer is crosslinked, and the carbon nanomaterial is dispersed into the water-soluble polymeric medium, and the water-soluble polymer is crosslinked. Thereby, formability or workability is improved.

After the crosslinking step, the water-soluble polymer which is used in the second step, and the water-soluble polymer of the different sort are mixed and are crosslinked, and thereby, the hardness adjustment of the material, or the control of conductivity, optical characteristics or the like, is possible.

The method for manufacturing the biocompatible electrode structure, may further include a rinse step in order to remove the molecules configuring the ionic liquid which are not bonded to the carbon nanomaterial. For example, the rinse step may be performed by the liquid which does not destroy physiological saline, ethanol, or the gel.

As described above, the study of the influence which the ionic liquid has on the living body is not sufficiently advanced, but in the method for manufacturing the biocompatible electrode structure, by including the rinse step, since the biocompatible electrode structure that covers the molecules configuring the ionic liquid which are bonded to the carbon nanomaterial with the water-soluble polymer is manufactured, the obtained biocompatible electrode structure prevents the molecules configuring the ionic liquid from touching the biological cell.

The rinse step may be performed at any stage, and for example, may be performed after the first step, after the second step, or after the step of manufacturing the biocompatible electrode structure.

By appropriately performing the rinse step after the first step, it is possible to surely make the molecules of the ionic liquid which cover the carbon nanomaterial into a monolayer. Moreover, by appropriately performing the rinse step after the second step or after the water-soluble polymer is crosslinked, it is possible to remove the molecules of the ionic liquid which are not bonded to the carbon nanomaterial. Since the water-soluble polymer is not dissolved after the crosslinking, it is easy to remove the molecules of the ionic liquid.

Method for Manufacturing Biocompatible Electrode Structure (Second Embodiment)

In the following description, there are cases where the contents which are described in the biocompatible electrode structure according to the first embodiment will be omitted if also applied to the present embodiment, and moreover, there are cases of being applied to the biocompatible electrode structure according to the first embodiment.

A method for manufacturing the biocompatible electrode structure according to the second embodiment, includes a step of forming a first polymeric medium that constitutes a first polymer layer which includes a conductive nanomaterial, on an electronic circuit which includes a plurality of electrodes, a process of forming a second polymeric medium that constitutes a second polymer layer which does not include the conductive nanomaterial or includes the conductive nanomaterial at a density which is lower than that of the first polymer layer, on the first polymeric medium, and a process of collectively processing the first polymeric medium and the second polymeric medium so as to be arranged on each electrode.

That is, a polymer gel into which the conductive nanomaterial is dispersed, is applied by one layer (first polymer layer) on the substrate including the electronic circuit, and a layer (second polymer layer) of the polymer gel that does not include the conductive nanomaterial or include the conductive nanomaterial at the density which is lower than that of the first polymer layer, is superimposed thereon, and thereafter, the gel layers of the two layers are processed by being crosslinked and being collectively patterned so as to be arranged on each electrode, and thereby, it is possible to manufacture a biocompatible electrode structure with a two-layer structure.

There are the following advantages of the method.

After one layer of the polymer gel layer is applied, and is crosslinked (cured), one more layer is to be applied, it is apt to peeling off due to weak adhesion, and in contrast thereto, in the case of the method, as an exemplary example, if two layers are stacked in a liquid phase state and are collectively cured, the adhesion is improved.

Moreover, when the biocompatible electrode structure is applied to a living body, since the gel layer (second polymer layer) of the side that touches the living body does not include carbon nanotubes or contains carbon nanotubes at a density which is lower than the density of the carbon nanotubes of the first polymer layer, the biocompatibility of the electrode becomes high.

Still more, since the second polymer layer that touches the living body does not include the carbon nanotube or contain the carbon nanotube at the density which is lower than the density of the carbon nanotube of the first polymer layer, it is possible to use the original softness of the gel, and can be applied to the living body. In comparison with the case where the conductive nanomaterial is uniformly included in the polymer gel layer, the amount of the conductive nanomaterial is small.

Furthermore, for example, there are the following advantages in the case where the carbon nanotube is used as a conductive nanomaterial.

Since the carbon nanotube is black, the accuracy of the patterning is dropped in the material including the carbon nanotube. In the case of the method, since the second polymer layer does not include carbon nanotubes or contains carbon nanotubes at a density which is lower than the density of the carbon nanotubes of the first polymer layer, it is easier to allow light to pass through than the first polymer layer. Accordingly, the accuracy of the patterning is improved by collectively pattering two layers.

<Device>

A device according to one embodiment of the present invention, is a device that includes the biocompatible electrode structure of the present invention as an electrode, and for example, may be used by being installed on the surface of a living body or inside a living body.

As a substrate where the electrode is formed, it is possible to use a sheet-shaped insulating base material. As an example, a commercially available polyimide film or poly- ethylene naphthalate film is used. The substrate may be used in a device according to another embodiment.

The device according to another embodiment of the present invention, is a device that includes the plurality of electrodes which are connected to the biocompatible electrode structure of the present invention, in which the biocompatible electrode structure is arranged for each electrode, and for example, may be used by being installed on the surface of a living body or inside a living body.

The device according to another embodiment of the present invention is a device that includes a plurality of electrodes, in which each electrode is configured by the first polymer layer which is configured by the polymeric medium including the conductive nanomaterial, and the second polymer layer that is configured by the polymeric medium which does not include the conductive nanomaterial or includes the conductive nanomaterial at a density which is lower than that of the first polymer layer is formed over the plurality of electrodes, and for example, may be used by being installed on the surface of a living body or in a living body.

The device according to another embodiment of the present invention is a device that includes the plurality of electrodes, in which each electrode is configured by the first polymer layer which is configured by the polymeric medium including the conductive nanomaterial, and the second polymer layer that is configured by the polymeric medium which does not include the conductive nanomaterial or includes the conductive nanomaterial at a density which is lower than the first polymer layer, and for example, may be used by being installed on the surface of a living body or inside a living body.

The device according to another embodiment of the present invention is a device that includes a plurality of electrodes which are connected to the biocompatible electrode structure of the present invention, in which respectively on each electrode, the first polymer layer which is configured by the polymeric medium including the conductive nanomaterial is arranged, and the second polymer layer that is configured by the polymeric medium which does not include the conductive nanomaterial or includes the conductive nanomaterial at a density which is lower than that of the first polymer layer covers the whole including the first polymer layer, and for example, may be used by being installed on the surface of a living body or inside a living body.

The device according to another embodiment of the present invention is a device that includes the plurality of electrodes which are connected to the biocompatible electrode structure of the present invention, in which per each electrode, the first polymer layer which is configured by the polymeric medium including the conductive nanomaterial, and the second polymer layer that is configured by the polymeric medium which does not include the conductive nanomaterial or includes the conductive nanomaterial at a density which is lower than that of the first polymer layer are arranged, and for example, may be used by being installed on the surface of a living body or inside a living body.

<Method for Manufacturing Device>

The device according to the present invention may be manufactured by forming the electronic circuit by using a known circuit making technology on the insulating base material, and forming the biocompatible electrode structure of the present invention, on the plurality of electrodes on the electronic circuit.

A method for manufacturing the device according to one embodiment of the present invention, includes a process of forming a first polymeric medium that becomes a first polymer layer which includes a conductive nanomaterial, on an electronic circuit which includes a plurality of electrodes, a process of forming a second polymeric medium that becomes a second polymer layer which does not include the conductive nanomaterial or includes the conductive nanomaterial at a density which is lower than the first polymer layer, on the first polymeric medium, and a process of collectively processing the first polymeric medium and the second polymeric medium so as to be arranged on each electrode.

Hereinafter, an example of the method for manufacturing the device according to one embodiment of the present invention will be described.

First, the sheet-shaped insulating base material having a predetermined shape is prepared. Specifically, for example, the commercially available polyimide film or the polyethylene naphthalate film is prepared.

Next, on one surface of the sheet-shaped insulating base material, by using the known circuit making technology, the electronic circuit (which includes the plurality of electrodes for arranging the biocompatible electrode structure) being the heart portion of the device is formed. As a known circuit making technology, for example, a flexible printed circuit board making technology is used. As a material of the electrode, it is preferable that the metallic material such as gold or platinum which is unlikely to corrode is used. In the example, there is the configuration in which the biocompatible electrode structure is arranged on the electrode which is configured of the material, but the biocompatible electrode structure itself may be used as an electrode.

Next, in the sheet-shaped insulating base material where the circuit is formed, a layer which is configured by a first insulating material is formed which exposes the plurality of electrodes and a periphery portion thereof. The material of the first insulating material is not limited, and for example, it is possible to use parylene (registered trademark) or CYTOP (registered trademark). For example, parylene may be covered by a CVD method, and moreover, CYTOP may be covered by dipping.

For example, the thickness of the covered layer of the first insulating material is 1 µm to 10 µm.

Subsequently, the polymer gel including the conductive nanomaterial (for example, the composition that is made by dispersing carbon nanotubes which are covered with the molecules configuring N,N-diethyl-N-methyl-N-(2-methoxyethyl) ammonium tetrafluoroborate (DEMEBF$_4$) shown in FIG. 4A into polyrotaxane (which includes the photocrosslinking agent)) is applied thereon. Thereby, a state where the polymer gel layer which forms the first polymer layer is applied on the covered layer of the first insulating material, and on a region (the plurality of electrodes and the periphery portion thereof) where it is not covered, is achieved.

Next, in the polymer gel, the polymer gel layers of two layers are formed by applying the polymer gel which does not include the conductive nanomaterial or of which the density of the conductive nanomaterial is lower than that of the polymer gel, on the polymer gel layer.

Subsequently, for example, ultrafine digital type UV exposure system ("digital exposure apparatus", which is manufactured by PMT Corporation) is used, and the photocrosslinking is performed, and the patterning is performed so that the polymer layers of two layers are arranged on each electrode, and the biocompatible electrode structure is manufactured on each electrode.

Next, a second insulating material such as parylene is wholly covered, and the second insulating material on the biocompatible electrode structure is removed by using a laser beam or the like, and the biocompatible electrode structure is exposed.

In summary, by the above processes, it is possible to manufacture the device.

The sheet-shaped insulating base material may be attached to a support substrate such as a flat glass substrate.

Figure 3:
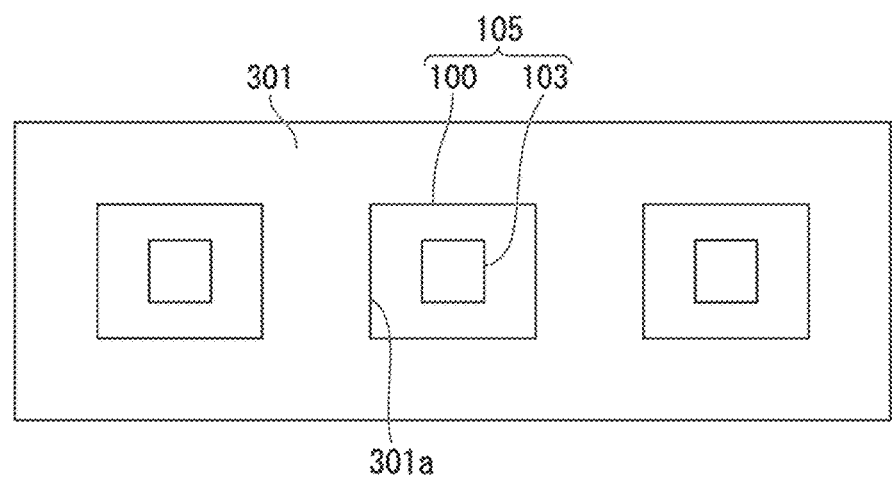
FIG. 3 is a schematic view for showing another example of a method for arranging the biocompatible electrode structure on a plurality of electrodes of an electronic circuit, in manufacturing of the device of the present invention.

FIG. 3 is a schematic view for showing another example of the embodiment of a method for arranging the biocompatible electrode structure on the plurality of electrodes of the electronic circuit, in manufacturing of the device of the present invention.

After the electronic circuit is formed by using the known circuit making technology on one surface of the insulating base material (not shown), all of the electronic circuit is included, and one surface of the insulating base material is covered with a rubber 301. As a rubber, for example, silicon rubber or fluorine rubber may be used. The rubber is preferably a hydrophobic rubber. As a method for covering one surface of the insulating base material which includes all of the electronic circuit, there is no limit in particular.

Next, regarding the rubber, by making the patterning at a spot where the electrode is arranged (for example, by making patterning into a lattice shape), a hole 301a is open.

Next, by embedding an electrode member 105 which is manufactured in advance by accumulating the biocompatible electrode structure 100 of the present invention on the electrode 103 into the hole 301a, the electrode portion of the device is manufactured.

Hereinafter, the present invention will be specifically described on the basis of Examples. However, Examples are thoroughly disclosed as an aid for easily understanding the present invention, and the present invention is not limited thereto.

Examples

Figure 4:
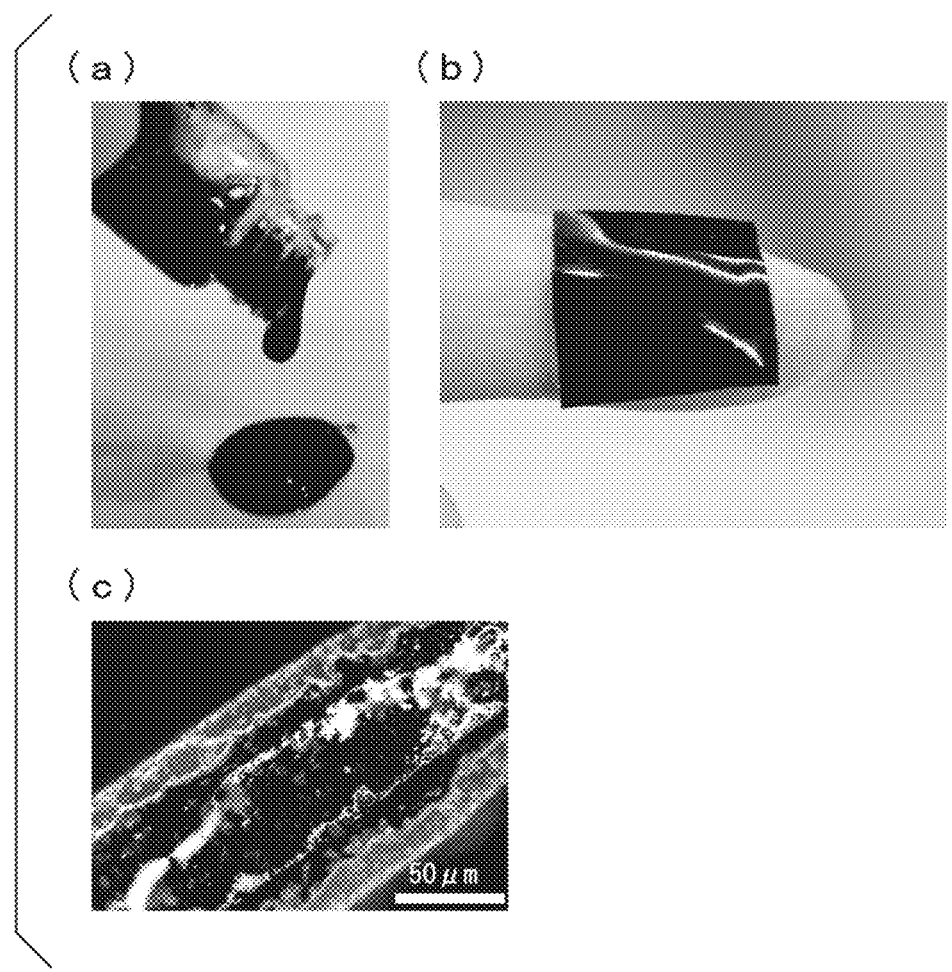
FIG. 4(a) is a photograph showing a composition that is configured by dispersing carbon nanotube which is covered with molecules configuring $DEMEBF_4$ into polyrotaxane.
FIG. 4(b) is a photograph of a sheet that is obtained by photocrosslinking the composition shown in FIG. 4(a).
FIG. 4(c) is an optical microscope photograph of a case where the composition shown in FIG. 4(a) is photocrosslinked, and a microstructure of a line width of approximately 50 μm is patterned.

FIG. 4(a) is a photograph showing the state before the composition that is made by dispersing the carbon nanotube which is covered with the molecules configuring N,N-diethyl-N-methyl-N-(2-methoxyethyl) ammonium tetrafluoroborate (DEMEBF$_4$) into polyrotaxane is cured by ultraviolet rays (UV). It is found out that the obtained composition has a gel shape. In the present specification, "gel shape" is a designation with respect to a liquid shape having fluidity, and means a state where the fluidity is lost, or a state where the fluidity is substantially lost.

The biocompatible electrode structure according to the present invention may be manufactured by using the composition. That is, the composition is applied on the electronic circuit, and the carbon nanotube is unevenly distributed using a magnet from below, and it is possible to manufacture a biocompatibility electrode structure by curing that. Moreover, the composition is applied on the electronic circuit, and thereon, a layer which is configured by only polyrotaxane is stacked, and it is possible to manufacture the biocompatible electrode structure by patterning that.

The composition is manufactured in the following manner. First, 30 mg of the commercially available carbon nanotube (MWNT, length 10 µm, diameter 5 nm), and 60 ng of N,N-diethyl-N-methyl-N-(2-methoxyethyl) ammonium tetrafluoroborate (DEMEBF$_4$) being the hydrophilic ionic liquid are mixed, and are stirred for one week at at 700 rpm or more by using a magnetic stirrer in the deionized water of 25° C. Subsequently, the obtained suspension is treated by using a high-pressure jet mill homogenizer (60 MPa; Nanojet pal, JN10, Jokoh), and a solution including CNT gel of black color is obtained. After the solution including the obtained CNT gel is rinsed with physiological saline, 1 mg of the photocrosslinking agent (Irgacure 2959, which is manufactured by Nagase & Co., Ltd.), and 1000 mg of polyrotaxane gel ("photocrosslinkable ring motion gel", which is manufactured by Advanced Softmaterials Inc.) are mixed, and the composition is manufactured.

FIG. 4(b) is a photograph of a sheet that is cured by making the irradiation with ultraviolet rays (wavelength: 365 nm) for five minutes, with respect to the composition shown in FIG. 4(a). Young's modulus of the cured sheet is lower than 10 kPa. Since Young's modulus of silicon is approximately 100 GPa, and Young's modulus of plastic film of the related art is 1 GPa to 5 GPa, in contrast thereto, it is found out that the sheet is particularly soft. Moreover, since Young's modulus of the brain is 1 kPa to 2 kPa, and Young' modulus of a muscle cell of the heart is to 100 kPa, it was found out that the material of the biocompatible electrode structure of one embodiment of the present invention, is a material having softness which is approximately the same as the internal organ or the softness or more. Therefore, high followability is included on the surface of the internal organ, and it is possible to form the very good interface between the internal organs.

FIG. 4(c) is an optical microscope photograph of a case where the ultrafine digital type UV exposure system ("digital exposure apparatus", which is manufactured by PMT Corporation) is used, and the photocrosslinking is performed, and a microstructure of a line width of approximately 50 μm is patterned. In this manner, the material of the biocompatible electrode structure of one embodiment of the present invention is a material in which the fine process is possible. Since the crosslinking depending on electromagnetic waves of various wavelengths may be realized by changing the sort of the photocrosslinking material, in the embodiment, UV is used as an electromagnetic wave with which the composition is cured, but it is limited thereto.

Figure 5:
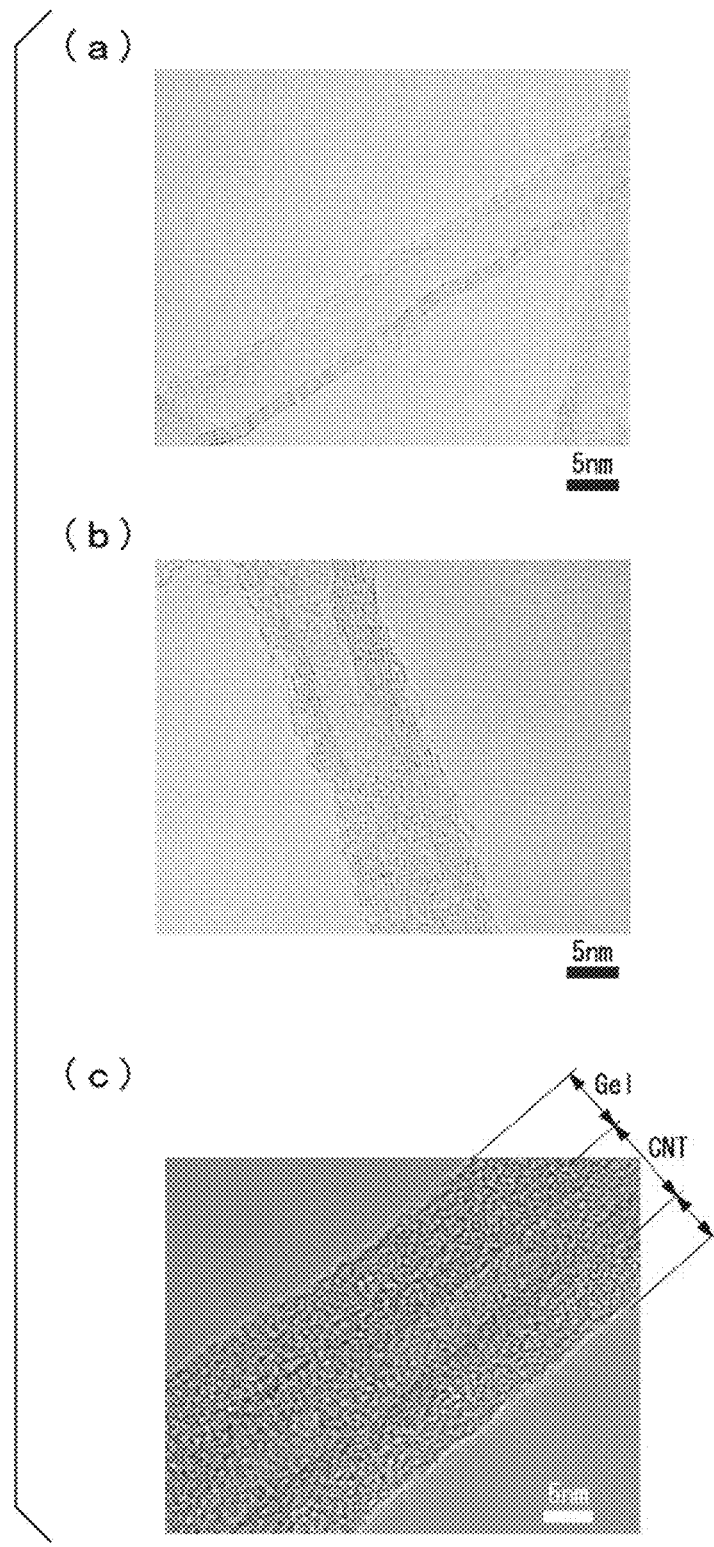
FIG. 5(a) is a TEM image of the carbon nanotube which is capable of being used in the present invention.
FIG. 5(b) is a TEM image of the carbon nanotube that is covered with polyrotaxane which is obtained in a case where the carbon nanotube and polyrotaxane are mixed in water without an ionic liquid, and are stirred while subdivision is performed in a jet mill.
FIG. 5(c) is a TEM image of a carbon nanomaterial or a composition which is obtained under the same condition as the composition shown in FIG. 4(a).

FIG. 5(a) to FIG. 5(c) are high resolution cross-sectional transmission electron microscope images (TEM images). FIG. 5(a) is a TEM image of the carbon nanotube (MWNT, length 10 μm, diameter 5 nm) which is capable of being used in the present invention. FIG. 5(b) is a TEM image of the carbon nanotube that is covered with polyrotaxane which is obtained in a case where 30 mg of the carbon nanotube (MWNT, length 10 μm, diameter 5 nm), and 100 mg of polyrotaxane ("photocrosslinkable ring motion gel", which is manufactured by Advanced Softmaterials Inc.) are mixed in water without the ionic liquid, and are stirred while the subdivision is performed in the jet mill. FIG. 5(c) shows a TEM image of the composition which is manufactured under the same condition as that shown in FIG. 5(a). As a high resolution cross-sectional transmission electron microscope, HF-2000Cold-FE TEM (80 kV, which is manufactured by Hitachi High-Technologies Corporation) is used.

As shown in FIG. 5(a), the carbon nanotube which is used in Examples, is configured of three layers or four layers. As shown in FIG. 5(b), the carbon nanotube of the simple substance is covered by polyrotaxane, but it was found out that the thickness of the covered layer is not uniform. In contrast thereto, as shown in FIG. 5(c), it was discovered that the thickness of the polyrotaxane layer which covers the carbon nanotube of the simple substance is uniform, and is clearly different from that shown in FIG. 5(b).

The difference of uniformity relating to the thickness of the covered layers, illustrates that the latter is not the layer in which the molecules of the hydrophilic ionic liquid DEMEBF$_4$ covering the carbon nanotube are peeled off, and polyrotaxane covers the carbon nanotube, but a layer in which polyrotaxane is covered on the layer of the molecules of the hydrophilic ionic liquid DEMEBF$_4$ covering the carbon nanotube. If the molecules of the hydrophilic ionic liquid DEMEBF$_4$ covering the carbon nanotube are peeled off, and polyrotaxane covers the carbon nanotube, in FIG. 5(c), the layer thickness of the covered layer is not uniform in the same manner as FIG. 5(b). Moreover, since the carbon nanotube and the bonding of the molecule of DEMEBF$_4$ are bonded by the high cation-π interaction which is equal to hydrogen bond, it is considered that the molecules of the hydrophilic ionic liquid DEMEBF$_4$ covering the carbon nanotube are not peeled off in the above processes.

Figure 6:
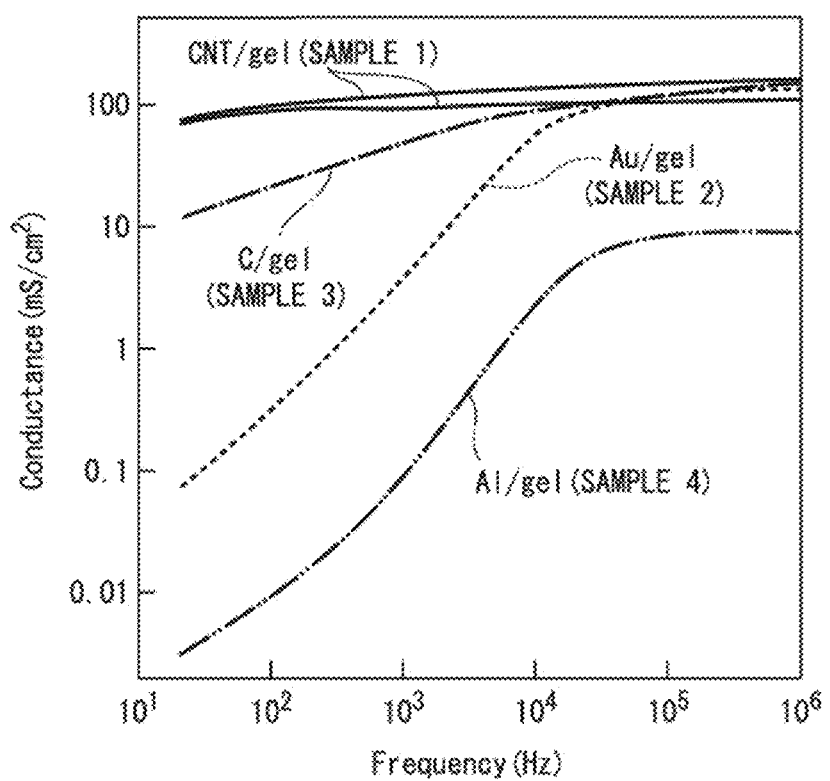
FIG. 6 is a graph showing frequency dependency of conductance of the biocompatible electrode structure of the present invention.

FIG. 6 is a graph showing frequency dependency of conductance (real number portion of a reciprocal number of the impedance) of the two-layered structure of the polyrotaxane layer (which is equivalent to the first polymer layer (reference sign 203 of FIG. 2)) into which the carbon nanotube is dispersed, and the polyrotaxane layer (which is equivalent to the second polymer layer (reference sign 204 of FIG. 2)) which does not contain the carbon nanotube. A horizontal axis of the graph shows the frequency (Frequency [Hz]) of the electrical signal, and a vertical axis shows the conductance (Conductance [mS/cm$^2$]).

A solid line of the graph is related to Sample 1 in which the polymeric medium of the two-layered structure according to the present invention is stacked on Au (gold). A dashed line is related to Sample 2 in which the polyrotaxane layer which does not contain the carbon nanotube is stacked on Au. A one-dot chain line is related to Sample 3 in which the polyrotaxane layer which does not contain the carbon nanotube is stacked on carbon. A two-dot chain line is related to Sample 4 in which the polyrotaxane layer which does not contain the carbon nanotube is stacked on Al (aluminum).

Furthermore, although being not shown in the graph, the polyrotaxane layer where the carbon nanotube is uniformly dispersed at the density which is lower than the first polymer layer of Sample 1, obtains the frequency characteristics of the conductance in the same manner as Sample 2 were obtained for. This is considered that there is no difference between the frequency characteristics, and the resistance R is low on the side of the polyrotaxane layer where the carbon nanotubes are uniformly distributed.

Sample 1 is manufactured as follows.

30 mg of the commercially available carbon nanotube (MWNT, length 10 μm, diameter 5 nm), and 60 mg of N,N-diethyl-N-methyl-N-(2-methoxyethyl) ammonium tetrafluoroborate (DEMEBF$_4$) being the hydrophilic ionic liquid are mixed, and are stirred for one week at rotation number of 700 rpm or more by using the magnetic stirrer in the deionized water of 25° C. The obtained suspension is treated by using the high-pressure jet mill homogenizer (60 MPa; Nano-jet pal, JN10, Jokoh), and a black material is obtained. After the solution including the obtained CNT gel is rinsed with physiological saline, 1 mg of the photocrosslinking agent (Irgacure 2959, which is manufactured by Nagase & Co., Ltd.), and 1000 mg of polyrotaxane gel ("photocrosslinkable ring motion gel", which is manufactured by Advanced Softmaterials Inc.) are mixed, and the composition shown in FIG. 4A is manufactured. A gel layer which is equivalent to the first polymer layer is formed by applying the composition on Au. Next, on the gel layer, 5 mg of the above photocrosslink agent, and 5000 mg of the above polyrotaxane gel are mixed, and the layer of the polyrotaxane gel is stacked. Next, the gel layers of two layers are irradiated with ultraviolet rays (wafelength: 365 nm), and are cured, and Sample 1 is obtained.

Sample 2 is obtained by that on Au, the layer of the polyrotaxane gel is formed by mixing 5 mg of the above photocrosslinking agent and 5000 mg of the above polyrotaxane gel, and subsequently, is irradiated with ultraviolet rays (wafelength: 365 nm), and is cured.

Sample 3 is obtained by that on carbon, the layer of the polyrotaxane gel is formed by mixing 5 mg of the above photocrosslinking agent and 5000 mg of the above polyrotaxane gel, and subsequently, is irradiated with ultraviolet rays (wafelength: 365 nm), and is cured.

Sample 4 is obtained by that on Aluminum, the layer of the polyrotaxane gel is formed by mixing 5 mg of the above photocrosslinking agent and 5000 mg of the above polyrotaxane gel, and subsequently, is irradiated with ultraviolet rays (wafelength: 365 nm), and is cured.

In all of Samples 2 to 4 where the polyrotaxane layer which does not contain the carbon nanotube is stacked, the frequency becomes low in the low frequency region, and the tendency that the conductance is reduced is shown. On the other hand, in Sample 1 according to the present invention, there is no frequency dependence in the low frequency region, and the tendency that the conductance is substantially fixed in the same manner as the high frequency region, is shown.

It is found out that Sample 1 according to the present invention, has the conductance which is great as approximately one digit in comparison with Sample 2 in the low frequency region, and which is great as two digits to three digits or more in comparison with Samples 3 and 4.

From the results, by making the polymeric medium of the two-layered structure according to the present invention, it was found out that the transmission performance of the electrical signal is greatly improved.

The mechanism is not clear, but in Sample 2, and, all of the polymer layers into which the carbon nanotube is uniformly dispersed, the lowering of the conductance is observed at the peculiar frequency of the capacitor, and on the other hand, in the polymeric medium of the two-layered structure according to the present invention, the lowering of the conductance is not observed even at the low frequency, and it is shown to be configured such that the entirely different transmission mechanism is dominant.

Figure 7:
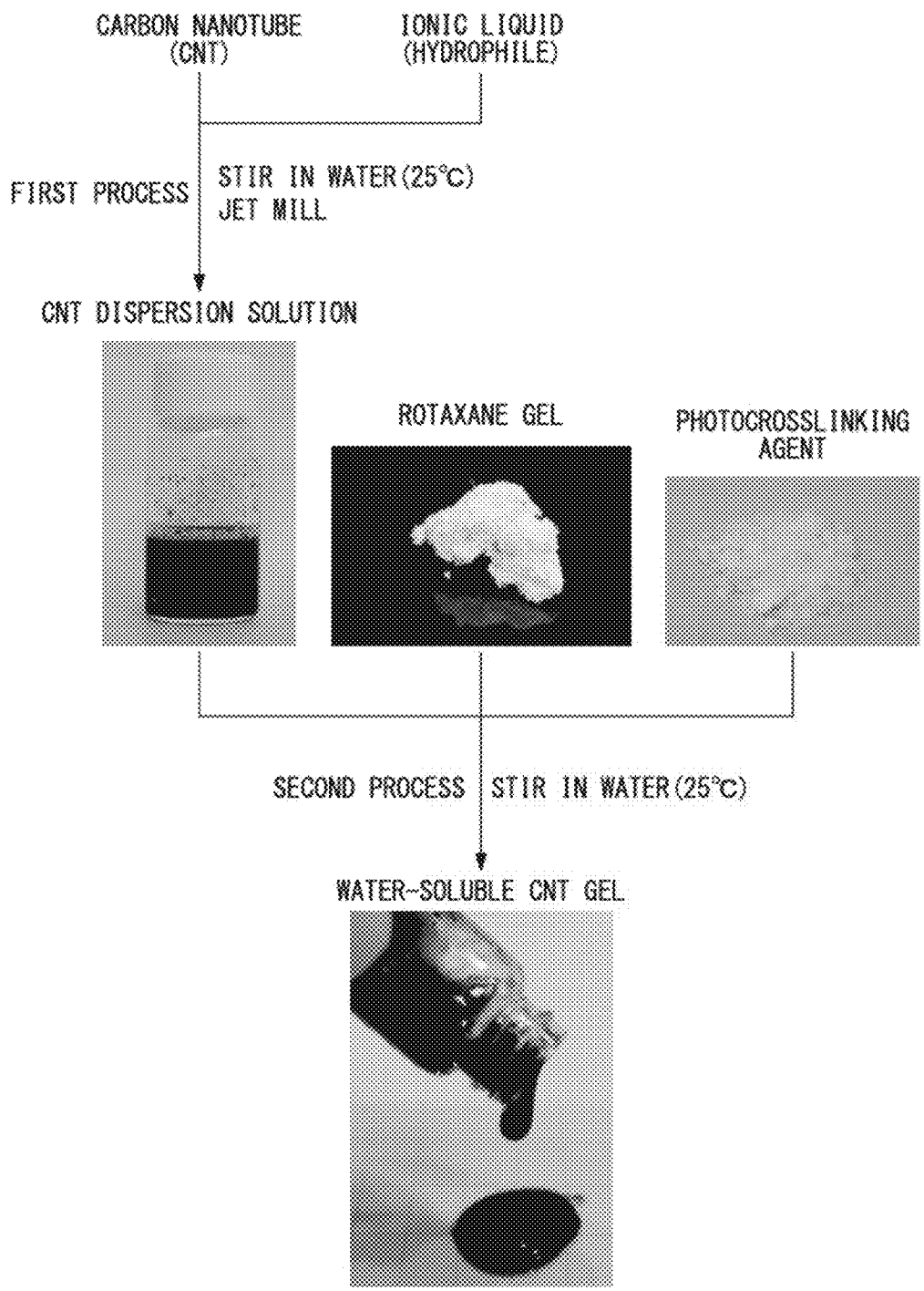
FIG. 7 is a flowchart showing a method for manufacturing a composition being a raw material of a first polymer layer which configures the biocompatible electrode structure of the present invention.
Figure 8:
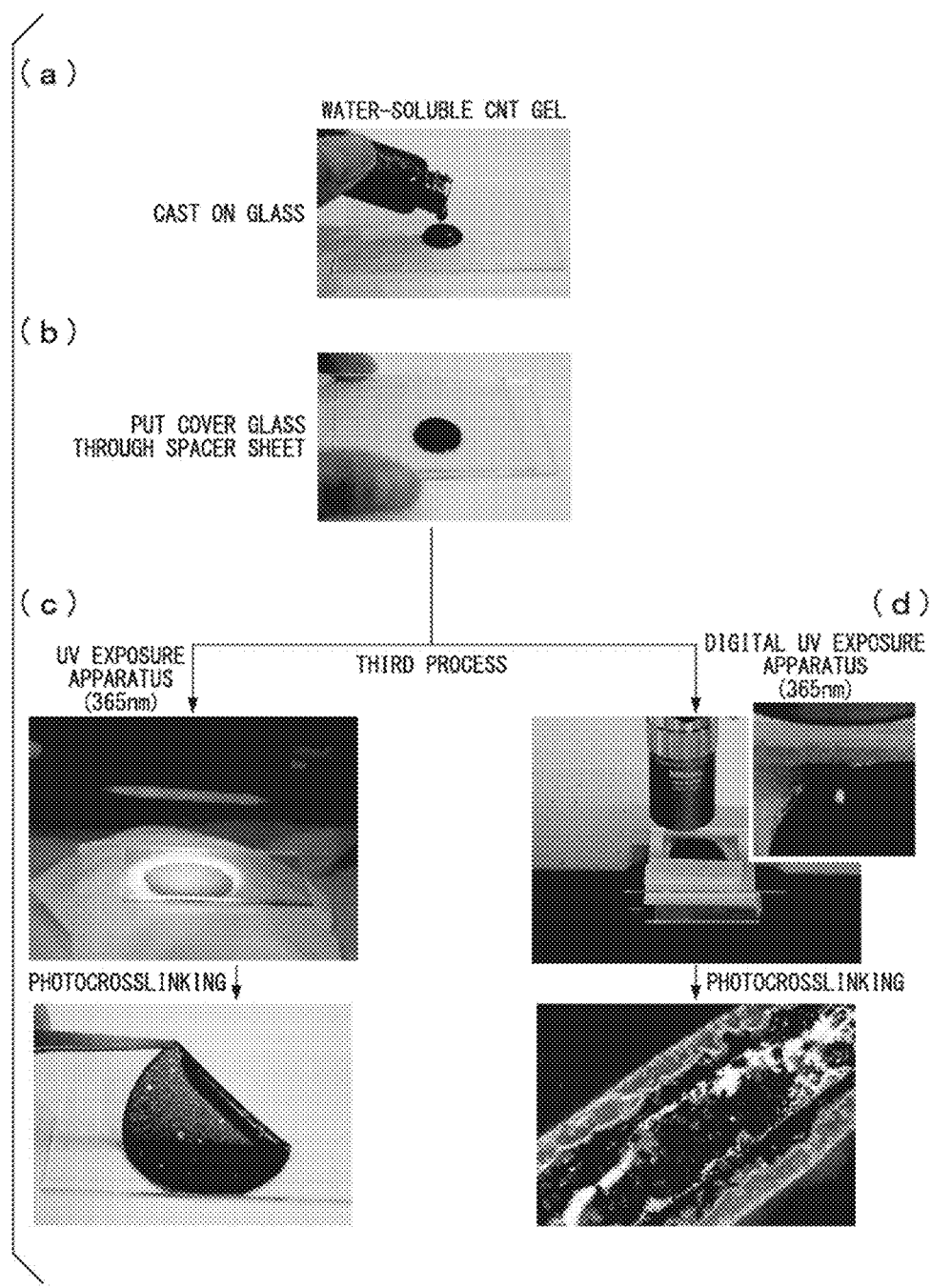
FIG. 8 is a flowchart showing a method for manufacturing the first polymer layer which configures the biocompatible electrode structure of the present invention.

In the following, the manufacturing method of the first polymer layer forming the biocompatible electrode structure of the present invention will be described with reference to FIG. 7 and FIG. 8 using a case where carbon nanotubes, N,N-diethyl-N-methyl-N-(2-methoxyethyl) ammonium tetrafluoroborate ($DEMEBF_4$), and polyrotaxane were used as the carbon nanomaterial, the ionic liquid, and the water-soluble polymer respectively as an example.

(1) First Process

First, the carbon nanotubes, $DEMEBF_4$, and water were mixed and stirred together, thereby obtaining a first dispersed system in which the carbon nanotubes covered with molecules constituting the ionic liquid were dispersed. $DEMEBF_4$ which was not bonded to the carbon nanotubes may be removed by carrying out a rinsing process on the stirred first dispersed system using physiological saline, ethanol, a liquid which did not destroy a gel, or the like.

In the first dispersed system, there are cases in which the carbon nanotubes covered with the molecules constituting the ionic liquid were dispersed in water and, additionally, depending on the amount of the carbon nanotube and the ionic liquid, the carbon nanotubes which were not sufficiently covered or not covered with the molecules constituting the ionic liquid (including bundled carbon nanotubes) or the molecules constituting the ionic liquid were included.

In this process, it is preferable to subdivide the carbon nanotubes by applying a shear force to the carbon nanotubes using a jet mill or the like. This is because the subdivision causes the carbon nanotubes bundled due to the van der Waals force to divide into individual carbon nanotubes, the degree of bundling (aggregation) decreases, and it also becomes possible to separate the carbon nanotubes into individual pieces.

Figure 9:
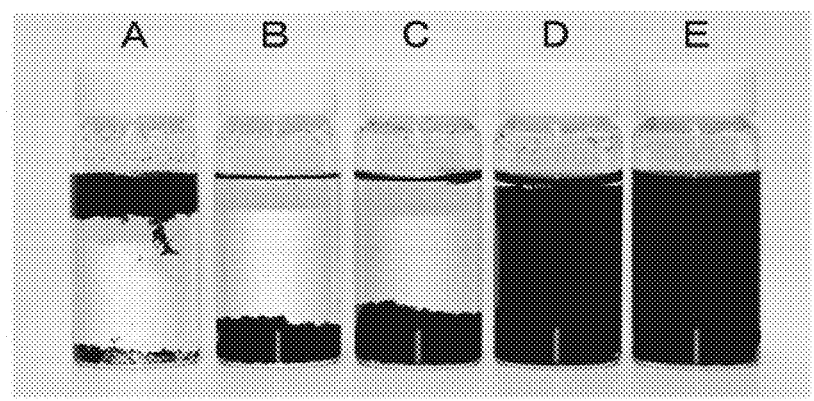
FIG. 9A to FIG. 9E are photographs showing a result from checking dispersibility of the carbon nanotube.

FIG. 9 shows the examination results of the dispersibility of the carbon nanotubes using five samples A to E. Sample A was a sample in a state where 30 mg of the carbon nanotubes was put into deionized water of 25° C. and was stirred for one week at a rotation speed of 700 rpm or higher using a magnetic stirrer. Sample B was a sample in a state where 30 mg of the carbon nanotubes and 60 mg of $DEMEBF_4$ were put into deionized water of 25° C. and were stirred for one week in the same manner. Sample C was a sample in a state where 30 mg of the carbon nanotubes was put into deionized water of 25° C., was stirred for one week in the same manner, and then were treated using a high-pressure jet mill homogenizer (60 MPa; Nano-jet pal, JN10, Jokoh). Sample D was a sample in a state where 30 mg of the carbon nanotubes and 60 mg of $DEMEBF_4$ were put into deionized water of 25° C., were stirred for one week in the same manner, and then were treated using a high-pressure jet mill homogenizer. Sample E was a sample in a state where 30 mg of the carbon nanotubes, 60 mg of $DEMEBF_4$, and microfibrillated cellulose (100 mg of 10% cellulose-containing aqueous solution, "CELISH (trade name)", manufactured by Daicel Chemical Industries Co., Ltd.) were put into deionized water of 25° C. and were stirred for one week in the same manner to obtain a paste, and then the paste was treated using a high-pressure jet mill homogenizer.

The "Celish (trade name)" is made from cellulose nanofibers which are microfibrillated through a special treatment method while having highly refined pure vegetable fibers as the raw material. The fibers constituting the raw material are torn into tens of thousands of fibers through this process, and the thickness of each fiber has been micronized within a range from 0.1 μm to 0.01 μm.

Compared to Samples A to C, the carbon nanotubes in Samples D and E have exhibited high water-dispersibility. From the result thereof, it has been found that it is effective to fragment the bundled carbon nanotubes by adding shear force in order to obtain high dispersibility.

(2) Second Process

Subsequently, the second dispersed system in which the carbon nanomaterials covered with molecules constituting the ion liquid, and the water-soluble polymers are dispersed is obtained by mixing and stirring the first dispersed system, polyrotaxane ("photo-crosslinkable cyclic dynamic gel", manufactured by Advanced Soft Materials Inc.), and water. The second dispersed system after being stirred may be subjected to a rinse process by using liquid or the like which does not destroy physiological saline, ethanol, and gel, thereby removing $DEMEBF_4$ which is not bound to the carbon nanotubes. As shown in FIG. 8, in a case of performing crosslinking of the obtained compositions, a crosslinking agent can also be mixed into the compositions. In this manner, the obtained second dispersed system can be a gel-like substance as shown in FIG. 8.

(3) Third Process

Subsequently, compositions (conductive materials) of crosslinked polyrotaxane is obtained by performing crosslinking of polyrotaxane and dispersing the carbon nanotubes covered with molecules constituting $DEMEBF_4$ into a polyrotaxane medium. The obtained compositions may be subjected to a rinse process by using liquid or the like which does not destroy physiological saline, ethanol, and gel, thereby removing $DEMEBF_4$ which is not bonded to the carbon nanotubes.

Hereinabove, description has been given regarding the process until the first polymer layer constituting a biocompatible electrode structure of the present invention is hardened.

Figure 10:
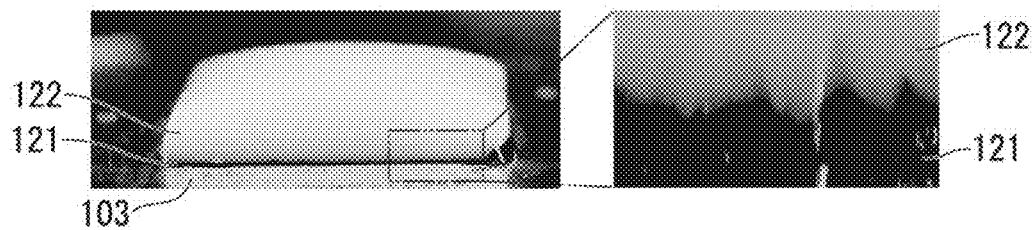
FIG. 10 is an optical microscope photograph of the biocompatible electrode structure of the present invention that is formed by stacking a layer which is formed by dispersing the carbon nanotube into polyrotaxane, and a layer of only polyrotaxane.

FIG. 10 is an optical microscopic photograph of a biocompatible electrode structure formed by stacking a layer which is obtained by dispersing the carbon nanotubes into polyrotaxane and a layer which is constituted by only polyrotaxane. The photograph on the right side is an enlarged photograph of a portion surrounded by the dotted line in the photograph on the left side.

The example shown in FIG. 10 is a substance in which a biocompatible electrode structure is formed on Au (a substance made through the same method as Sample 1 in FIG. 6). The layer indicated by the reference numeral 121 is a layer which is obtained by dispersing the carbon nanotubes into polyrotaxane, the layer indicated by the reference numeral 122 is a layer which is constituted by only polyrotaxane, and the reference numeral 103 indicates Au.

INDUSTRIAL APPLICABILITY

The present invention may provide the biocompatible structure, and the device including the same that have biocompatibility, and are capable of being inserted into the living body for the long period, and are capable of forming the extremely good interface between the internal organs by being excellent in followability with respect to the shape of the wrinkle of the internal organ, and have the low impedance throughout from the low frequency to the high frequency.

REFERENCE SIGNS LIST 100, 200 BIOCOMPATIBLE ELECTRODE STRUCTURE
100a CONNECTION SURFACE TO ELECTRONIC CIRCUIT
100b OPPOSITE SURFACE
101, 201 CONDUCTIVE NANOMATERIAL
102, 202 POLYMERIC MEDIUM
203 FIRST POLYMER LAYER
204 SECOND POLYMER LAYER

What is claimed is:

1. A biocompatible electrode structure which is capable of being connected to an electronic circuit, and in which a conductive nanomaterial is dispersed into at least one polymeric medium,
the biocompatible electrode structure comprising a first surface and a second surface,
wherein the first surface is on a connection surface side to the electronic circuit,
the second surface is on an opposite side of a connection surface to the electronic circuit, the second surface disposed so as to be able to contact a surface or a tissue of a living body, and
wherein a density of the conductive nanomaterial on the opposite side of a connection surface to the electronic circuit, in the polymeric medium is lower than that on the side of the connection surface to the electronic circuit, and
wherein the at least one polymeric medium is a water-soluble polymer and the at least one polymeric medium is a gel.

2. The biocompatible electrode structure according to claim 1,
wherein the conductive nanomaterial is a carbon nanomaterial.

3. The biocompatible electrode structure according to claim 1, wherein the water-soluble polymer dissolves or disperses in water.

4. The biocompatible electrode structure according to claim 1,
wherein the at least one polymeric medium comprises a first polymeric medium and a second polymeric medium, and
wherein the biocompatible electrode structure is formed by laminating a first polymer layer that is configured by the first polymeric medium which includes the conductive nanomaterial, and a second polymer layer that is configured by the second polymeric medium which does not include the conductive nanomaterial or includes the conductive nanomaterial at a density which is lower than the first polymer layer, in order from the side of the connection surface to the electronic circuit.

5. A device comprising:
the biocompatible electrode structure according to claim 1 as an electrode.

6. A device which includes the biocompatible electrode structure according to claim 1, comprising:
a plurality of electrodes that are connected to the biocompatible electrode structure,
wherein the biocompatible electrode structure is arranged according to the plurality of electrodes.

7. A device which includes the biocompatible electrode structure according to claim 4, comprising:
a plurality of electrodes,
wherein each electrode is configured by the first polymer layer, and
the second polymer layer is formed over the plurality of electrodes.

8. A device which includes the biocompatible electrode structure according to claim 4, comprising:
a plurality of electrodes,
wherein each electrode is configured by the first polymer layer and the second polymer layer.

9. A method for manufacturing the device according to claim 8, comprising:
a step of forming the first polymeric medium that becomes the first polymer layer which includes the conductive nanomaterial, on the electronic circuit;
a step of forming the second polymeric medium that becomes the second polymer layer which does not include the conductive nanomaterial or includes the conductive nanomaterial at a density which is lower than that of the first polymer layer, on the first polymeric medium; and
a step of collectively processing the first polymeric medium and the second polymeric medium so as to form a plurality of electrodes on the electronic circuit.

10. A device which includes the biocompatible electrode structure according to claim 4, comprising:
a plurality of electrodes that are connected to the biocompatible electrode structure,
wherein the first polymer layer is arranged for each electrode, and the second polymer layer is formed over the plurality of electrodes.

11. A device which includes the biocompatible electrode structure according to claim 4, comprising:
 a plurality of electrodes that are connected to the biocompatible electrode structure,
 wherein the first polymer layer and the second polymer layer are arranged for each electrode.

12. A method for manufacturing the device according to claim 11, comprising:
 a step of forming the first polymeric medium that constitutes the first polymer layer which includes the conductive nanomaterial, on an electronic circuit which includes a plurality of electrodes;
 a step of forming the second polymeric medium that constitutes the second polymer layer which does not include the conductive nanomaterial or includes the conductive nanomaterial at a density which is lower than that of the first polymer layer, on the first polymeric medium; and
 a step of collectively processing the first polymeric medium and the second polymeric medium so as to be arranged on each electrode.

13. A method for manufacturing the biocompatible electrode structure according to claim 1, comprising:
 a step of forming a liquid film which is configured by the at least one polymeric medium and the conductive nanomaterial is dispersed into the at least one polymeric medium, on an electronic circuit which includes a plurality of electrodes;
 a step of unevenly distributing the conductive nanomaterial of the at least one polymeric medium on the electronic circuit side; and
 a step of arranging the biocompatible electrode structure on each electrode by curing the liquid film.

14. A method for manufacturing the biocompatible electrode structure according to claim 4, comprising:
 a step of forming the first polymeric medium that constitutes the first polymer layer which includes a conductive nanomaterial, on an electronic circuit which includes a plurality of electrodes;
 a step of forming the second polymeric medium that constitutes the second polymer layer which does not include the conductive nanomaterial or includes the conductive nanomaterial at a density which is lower than the first polymer layer, on the first polymeric medium; and
 a step of collectively processing the first polymeric medium and the second polymeric medium so as to be arranged on each electrode.

\* \* \* \* \*